United States Patent
Min et al.

(10) Patent No.: US 9,951,363 B2
(45) Date of Patent: *Apr. 24, 2018

(54) ENZYMATIC HYDROLYSIS OF OLD CORRUGATED CARDBOARD (OCC) FINES FROM RECYCLED LINERBOARD MILL WASTE REJECTS

(71) Applicant: The Research Foundation for The State University of New York, Binghamton, NY (US)

(72) Inventors: Byeong Cheol Min, Syracuse, NY (US); Bhavin V. Bhayani, Syracuse, NY (US); Bandaru V. Ramarao, Fayetteveille, NY (US)

(73) Assignee: The Research Foundation for the State University of New York College of Environmental Science and Forestry, Syracuse, NY (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/656,988

(22) Filed: Mar. 13, 2015

(65) Prior Publication Data

US 2015/0259719 A1   Sep. 17, 2015

Related U.S. Application Data

(60) Provisional application No. 61/953,152, filed on Mar. 14, 2014.

(51) Int. Cl.
| | | |
|---|---|---|
| *C12P 19/14* | (2006.01) | |
| *C12P 19/02* | (2006.01) | |
| *C13K 1/02* | (2006.01) | |

(52) U.S. Cl.
CPC ............... *C12P 19/14* (2013.01); *C12P 19/02* (2013.01); *C13K 1/02* (2013.01)

(58) Field of Classification Search
CPC ............. C12P 19/14; C12P 19/02; C13K 1/02
See application file for complete search history.

(56) References Cited

U.S. PATENT DOCUMENTS

| | | |
|---|---|---|
| 3,990,944 A | 11/1976 | Gauss et al. |
| 4,017,642 A | 4/1977 | Orth, Jr. et al. |
| | (Continued) | |

FOREIGN PATENT DOCUMENTS

WO   WO 2012/112488   *   8/2012

OTHER PUBLICATIONS

Cui et al. Effect of Cellobiase and surfactant supplementation on the Enzymatic Hydrolysis of Pretreated Wheat Straw, BioResources (2011), vol. 6(4), pp. 3850-3858.*

(Continued)

*Primary Examiner* — Alexander D Kim
(74) *Attorney, Agent, or Firm* — Steven M. Hoffberg; Tully Rinckey PLLC

(57) ABSTRACT

A significant fraction of short fibers (fines) is produced while recycling Old Corrugated Containerboards (OCC), which are usually rejected as solid waste stream, requiring landfilling and posing environmental problems. The major component of these fines rejects are primarily cellulose that can be hydrolyzed into sugars for possible fermentation into biofuels, bioplastics or other sugar based products. Use of fines also offers benefits such as negative costs and production of fermentable sugars without requiring complex pretreatment processes, now required to hydrolyze and eliminate inhibitors from hydrolyzate. Enzymatic hydrolysis of reject fines from a recycled OCC mill, employing different strains of cellulases, were investigated. Fillers (up to 30 mass %) in the fines increases the required dosage of enzymes and costs. Enzyme loading can be lowered by addition of surfactants to reduce their inhibitory activity. The (Continued)

Enzymatic hydrolysis yield of different substrates. Enzyme was added 50 FPU of *T. reesei* and the hydrolysis was conducted at 50 °C for 3 days.

nonionic surfactant Triton X-80 improved hydrolysis yields by up to 10 percent points.

20 Claims, 9 Drawing Sheets

(56) References Cited

U.S. PATENT DOCUMENTS

| | | |
|---|---|---|
| 4,058,411 A | 11/1977 | Bellamy et al. |
| 4,235,968 A | 11/1980 | Pilipski |
| 4,260,685 A | 4/1981 | Pilipski |
| 4,275,163 A | 6/1981 | Gallo |
| 4,292,406 A | 9/1981 | Ljungdahl et al. |
| 4,321,278 A | 3/1982 | Johanning et al. |
| 4,321,328 A | 3/1982 | Hoge |
| 4,321,360 A | 3/1982 | Blount |
| 4,431,675 A | 2/1984 | Schroeder et al. |
| 4,540,587 A | 9/1985 | Gajewski |
| 4,594,130 A | 6/1986 | Chang et al. |
| 4,628,029 A | 12/1986 | Eveleigh et al. |
| 4,694,906 A | 9/1987 | Hutchins et al. |
| 4,713,118 A | 12/1987 | Barker et al. |
| 4,831,127 A | 5/1989 | Weibel |
| 4,851,394 A | 7/1989 | Kubodera |
| 4,950,597 A | 8/1990 | Saxena et al. |
| 4,975,459 A | 12/1990 | Mehta et al. |
| 5,023,275 A | 6/1991 | Amick |
| 5,037,663 A | 8/1991 | Dale |
| 5,055,308 A | 10/1991 | Fujinawa et al. |
| 5,059,654 A | 10/1991 | Hou et al. |
| 5,081,026 A | 1/1992 | Heikkila et al. |
| 5,091,399 A | 2/1992 | Osei-Gyimah et al. |
| 5,102,898 A | 4/1992 | Hsu |
| 5,112,382 A | 5/1992 | Hsu |
| 5,118,681 A | 6/1992 | Amick et al. |
| 5,149,524 A | 9/1992 | Sherba et al. |
| 5,151,447 A | 9/1992 | Amick |
| 5,166,390 A | 11/1992 | Weinstein et al. |
| 5,170,620 A | 12/1992 | Whistler et al. |
| 5,171,570 A | 12/1992 | Takemori et al. |
| 5,179,127 A | 1/1993 | Hsu |
| 5,198,074 A | 3/1993 | Villavicencio et al. |
| 5,292,762 A | 3/1994 | Hsu |
| 5,300,672 A | 4/1994 | Weinstein et al. |
| 5,302,592 A | 4/1994 | Osei-Gyimah et al. |
| 5,352,444 A | 10/1994 | Cox et al. |
| 5,391,561 A | 2/1995 | Hsu |
| 5,395,455 A | 3/1995 | Scott et al. |
| 5,395,623 A | 3/1995 | Kovach |
| 5,416,210 A | 5/1995 | Sherba et al. |
| 5,424,202 A | 6/1995 | Ingram et al. |
| 5,424,417 A | 6/1995 | Torget et al. |
| 5,437,992 A | 8/1995 | Bodie et al. |
| 5,458,899 A | 10/1995 | Floyd et al. |
| 5,464,832 A | 11/1995 | Osei-Gyimah et al. |
| 5,487,989 A | 1/1996 | Fowler et al. |
| 5,503,996 A | 4/1996 | Torget et al. |
| 5,505,950 A | 4/1996 | Floyd et al. |
| 5,518,902 A | 5/1996 | Ozaki et al. |
| 5,554,520 A | 9/1996 | Fowler et al. |
| 5,587,157 A | 12/1996 | Cox et al. |
| 5,589,164 A | 12/1996 | Cox et al. |
| 5,683,911 A | 11/1997 | Bodie et al. |
| 5,693,518 A | 12/1997 | Kofod et al. |
| 5,705,369 A | 1/1998 | Torget et al. |
| 5,733,758 A | 3/1998 | Nguyen |
| 5,736,032 A | 4/1998 | Cox et al. |
| 5,747,082 A | 5/1998 | Floyd et al. |
| 5,770,010 A | 6/1998 | Jelks |
| 5,786,313 A | 7/1998 | Schneider et al. |
| 5,792,630 A | 8/1998 | Tonouchi et al. |
| 5,861,271 A | 1/1999 | Fowler et al. |
| 5,863,783 A | 1/1999 | Van Heuvel et al. |
| 5,866,392 A | 2/1999 | Schou et al. |
| 5,871,550 A | 2/1999 | Goedegebuur et al. |
| 5,874,276 A | 2/1999 | Fowler et al. |
| 5,885,819 A | 3/1999 | Kofod et al. |
| 5,888,806 A | 3/1999 | Nguyen |
| 5,908,649 A | 6/1999 | Floyd et al. |
| 5,962,277 A | 10/1999 | Watanabe et al. |
| 5,962,278 A | 10/1999 | Tsuchida et al. |
| 5,989,887 A | 11/1999 | Van Heuvel et al. |
| 6,001,639 A | 12/1999 | Schulein et al. |
| 6,005,141 A | 12/1999 | Schneider et al. |
| 6,008,176 A | 12/1999 | Schneider et al. |
| 6,010,870 A | 1/2000 | Pelzer et al. |
| 6,013,490 A | 1/2000 | Kouda et al. |
| 6,017,740 A | 1/2000 | Kouda et al. |
| 6,048,715 A | 4/2000 | Haynes et al. |
| 6,069,136 A | 5/2000 | Tahara et al. |
| 6,074,856 A | 6/2000 | Wong et al. |
| 6,080,567 A | 6/2000 | Kofod et al. |
| 6,110,712 A | 8/2000 | Tsuchida et al. |
| 6,130,076 A | 10/2000 | Ingram |
| 6,132,998 A | 10/2000 | Naritomi et al. |
| 6,140,105 A | 10/2000 | Watanabe et al. |
| 6,153,413 A | 11/2000 | Watanabe et al. |
| 6,174,700 B1 | 1/2001 | Haynes et al. |
| 6,197,564 B1 | 3/2001 | Kofod et al. |
| 6,207,436 B1 | 3/2001 | Bjørnvad et al. |
| 6,228,630 B1 | 5/2001 | Kofod et al. |
| 6,268,196 B1 | 7/2001 | Fowler et al. |
| 6,268,197 B1 | 7/2001 | Schulein et al. |
| 6,309,871 B1 | 10/2001 | Outtrup et al. |
| 6,328,994 B1 | 12/2001 | Shimizu et al. |
| 6,333,181 B1 | 12/2001 | Ingram et al. |
| 6,361,989 B1 | 3/2002 | Svendsen et al. |
| 6,387,690 B1 | 5/2002 | Schulein et al. |
| 6,399,351 B1 | 6/2002 | Bjørnvad et al. |
| 6,420,165 B1 | 7/2002 | Weinstein et al. |
| 6,444,653 B1 | 9/2002 | Huppe et al. |
| 6,451,063 B1 | 9/2002 | Clarkson et al. |
| 6,500,658 B1 | 12/2002 | Wu et al. |
| 6,528,298 B1 | 3/2003 | Svendsen et al. |
| 6,555,228 B2 | 4/2003 | Guritza |
| 6,555,335 B1 | 4/2003 | Saloheimo et al. |
| 6,566,114 B1 | 5/2003 | Kauppinen et al. |
| 6,620,605 B2 | 9/2003 | Fowler et al. |
| 6,623,948 B1 | 9/2003 | Outtrup et al. |
| 6,630,340 B2 | 10/2003 | Wilting et al. |
| 6,663,780 B2 | 12/2003 | Heikkila et al. |
| 6,713,460 B2 | 3/2004 | Huppe et al. |
| 6,768,001 B2 | 7/2004 | Saloheimo et al. |
| 6,815,192 B2 | 11/2004 | Schnorr et al. |
| 6,818,434 B2 | 11/2004 | Watanabe et al. |
| 6,855,531 B2 | 2/2005 | Shulein et al. |
| 6,878,199 B2 | 4/2005 | Bowden et al. |
| 6,894,199 B2 | 5/2005 | Heikkila et al. |
| 6,908,995 B2 | 6/2005 | Blount |
| 6,911,565 B2 | 6/2005 | Heikkila et al. |
| 6,942,754 B2 | 9/2005 | Izumi et al. |
| 6,982,159 B2 | 1/2006 | Dunn-Coleman et al. |
| 7,005,289 B2 | 2/2006 | Dunn-Coleman et al. |
| 7,033,811 B2 | 4/2006 | Rey et al. |
| 7,045,331 B2 | 5/2006 | Dunn-Coleman et al. |
| 7,045,332 B2 | 5/2006 | Dunn-Coleman et al. |
| 7,048,952 B2 | 5/2006 | Gerson et al. |
| 7,049,125 B2 | 5/2006 | Dunn-Coleman et al. |
| 7,056,721 B2 | 6/2006 | Dunn-Coleman et al. |
| 7,067,303 B1 | 6/2006 | Nichols et al. |
| 7,070,805 B2 | 7/2006 | Shimizu et al. |
| 7,083,673 B2 | 8/2006 | Bowden et al. |
| 7,109,005 B2 | 9/2006 | Eroma et al. |
| 7,144,716 B2 | 12/2006 | Saville et al. |
| 7,172,891 B2 | 2/2007 | Rey et al. |
| 7,183,093 B2 | 2/2007 | Kauppinen et al. |
| 7,198,925 B2 | 4/2007 | Foody |
| 7,226,772 B2 | 6/2007 | Hseu et al. |
| 7,226,773 B2 | 6/2007 | Schulein et al. |
| 7,273,742 B2 | 9/2007 | Dunn-Coleman et al. |
| 7,320,886 B2 | 1/2008 | Dunn-Coleman et al. |
| 7,344,871 B2 | 3/2008 | Dunn-Coleman et al. |
| 7,344,876 B2 | 3/2008 | Levine |
| 7,351,568 B2 | 4/2008 | Dunn-Coleman et al. |

(56) References Cited

U.S. PATENT DOCUMENTS

| | | |
|---|---|---|
| 7,351,573 B2 | 4/2008 | Dunn-Coleman et al. |
| 7,361,736 B2 | 4/2008 | Schnorr et al. |
| 7,381,553 B2 | 6/2008 | Zhao et al. |
| 7,399,485 B1 | 7/2008 | Shimizu et al. |
| 7,399,855 B2 | 7/2008 | Frost |
| 7,407,788 B2 | 8/2008 | Dunn-Coleman et al. |
| 7,431,942 B2 | 10/2008 | Shimizu et al. |
| 7,449,319 B2 | 11/2008 | Dunn-Coleman et al. |
| 7,449,550 B2 | 11/2008 | Adney et al. |
| 7,452,707 B2 | 11/2008 | Goedegebuur et al. |
| 7,459,299 B2 | 12/2008 | Goedegebuur et al. |
| 7,503,981 B2 | 3/2009 | Wyman et al. |
| 7,504,120 B2 | 3/2009 | Steer et al. |
| 7,527,959 B2 | 5/2009 | Dunn-Coleman et al. |
| 7,547,534 B2 | 6/2009 | Steer et al. |
| 7,566,561 B2 | 7/2009 | Svendsen et al. |
| 7,582,462 B2 | 9/2009 | Dunn-Coleman et al. |
| 7,585,652 B2 | 9/2009 | Foody et al. |
| 7,592,163 B2 | 9/2009 | Zhao et al. |
| 7,592,434 B2 | 9/2009 | Kerovuo et al. |
| 7,601,529 B2 | 10/2009 | Glad et al. |
| 7,611,882 B2 | 11/2009 | Bjornvad et al. |
| 7,625,728 B2 | 12/2009 | Eroma et al. |
| 7,632,479 B2 | 12/2009 | Curren et al. |
| 7,642,079 B2 | 1/2010 | Cayouette et al. |
| 7,651,582 B2 | 1/2010 | Weimer et al. |
| 7,659,099 B2 | 2/2010 | Saville et al. |
| 7,670,813 B2 | 3/2010 | Foody et al. |
| 7,682,811 B2 | 3/2010 | Leschine et al. |
| 7,709,697 B2 | 5/2010 | Raab |
| 7,723,568 B2 | 5/2010 | Lutfiyya et al. |
| 7,727,746 B2 | 6/2010 | Foody et al. |
| 7,727,754 B2 | 6/2010 | Dunn-Coleman et al. |
| 7,732,173 B2 | 6/2010 | Mairal et al. |
| 7,741,089 B2 | 6/2010 | Hitchman et al. |
| 7,754,457 B2 | 7/2010 | Foody et al. |
| 7,781,191 B2 | 8/2010 | Dunson, Jr. et al. |
| 7,785,854 B2 | 8/2010 | St-Pierre et al. |
| 7,786,350 B2 | 8/2010 | Allen et al. |
| 7,786,351 B2 | 8/2010 | Houmard et al. |
| 7,803,601 B2 | 9/2010 | Nobles, Jr. et al. |
| 7,807,419 B2 | 10/2010 | Hennessey et al. |
| 7,807,434 B2 | 10/2010 | Dunn-Coleman et al. |
| 7,810,507 B2 | 10/2010 | Dube et al. |
| 7,811,799 B2 | 10/2010 | Dunn-Coleman et al. |
| 7,816,581 B2 | 10/2010 | Gilbertson et al. |
| 7,819,976 B2 | 10/2010 | Friend et al. |
| 7,829,732 B2 | 11/2010 | Mascal |
| 7,838,666 B2 | 11/2010 | Yaginuma et al. |
| 7,846,705 B2 | 12/2010 | Kensch et al. |
| 7,867,745 B2 | 1/2011 | Hansen et al. |
| 7,875,292 B2 | 1/2011 | Shimizu et al. |
| 7,887,862 B2 | 2/2011 | Paz Briz et al. |
| 7,901,511 B2 | 3/2011 | Griffin et al. |
| 7,906,704 B2 | 3/2011 | Raab |
| 7,910,338 B2 | 3/2011 | Hennessey et al. |
| 7,910,347 B1 | 3/2011 | DiCosimo et al. |
| 7,923,233 B1 | 4/2011 | Dicosimo et al. |
| 7,923,235 B2 | 4/2011 | Foreman et al. |
| 7,923,236 B2 | 4/2011 | Gusakov et al. |
| 7,927,854 B1 | 4/2011 | DiCosimo et al. |
| 7,931,784 B2 | 4/2011 | Medoff |
| 7,932,063 B2 | 4/2011 | Dunson, Jr. et al. |
| 7,932,065 B2 | 4/2011 | Medoff |
| 7,932,072 B1 | 4/2011 | DiCosimo et al. |
| 7,939,488 B2 | 5/2011 | Scheuing et al. |
| 7,943,363 B2 | 5/2011 | Blanchard et al. |
| 7,946,295 B2 | 5/2011 | Brinkley et al. |
| 7,947,813 B2 | 5/2011 | Fahrner et al. |
| 7,951,570 B2 | 5/2011 | Goedegebuur et al. |
| 7,951,571 B2 | 5/2011 | Goedegebuur et al. |
| 7,954,734 B2 | 6/2011 | Hata |
| 7,960,146 B2 | 6/2011 | Dunn-Coleman et al. |
| 7,960,148 B2 | 6/2011 | Steer et al. |
| 7,960,151 B1 | 6/2011 | DiCosimo et al. |
| 7,960,153 B2 | 6/2011 | Czechowski et al. |
| 7,960,160 B2 | 6/2011 | Yaver et al. |
| 7,960,528 B1 | 6/2011 | DiCosimo et al. |
| 7,964,383 B1 | 6/2011 | DiCosimo et al. |
| 7,967,904 B2 | 6/2011 | Bowden et al. |
| 7,972,832 B2 | 7/2011 | Day et al. |
| 7,977,450 B2 | 7/2011 | Frost |
| 7,981,643 B2 | 7/2011 | Dicosimo et al. |
| 7,981,644 B2 | 7/2011 | Dicosimo et al. |
| 7,981,646 B2 | 7/2011 | Heald et al. |
| 7,993,463 B2 | 8/2011 | Griffin et al. |
| 7,993,890 B2 | 8/2011 | Soerensen et al. |
| 7,993,898 B2 | 8/2011 | Andersen et al. |
| 7,998,711 B2 | 8/2011 | Goedegebuur et al. |
| 7,998,713 B2 | 8/2011 | Dunson, Jr. et al. |
| 8,008,056 B2 | 8/2011 | Aehle et al. |
| 8,017,372 B2 | 9/2011 | Andersen et al. |
| 8,017,820 B2 | 9/2011 | Foody et al. |
| 8,030,050 B2 | 10/2011 | Berg et al. |
| 8,034,592 B2 | 10/2011 | Elias et al. |
| 8,043,837 B2 | 10/2011 | Burke et al. |
| 8,043,839 B2 | 10/2011 | Weiner et al. |
| 8,053,566 B2 | 11/2011 | Belanger et al. |
| 8,061,362 B2 | 11/2011 | Mua et al. |
| 8,063,201 B2 | 11/2011 | Medoff |
| 8,067,222 B2 | 11/2011 | Kerovuo et al. |
| 8,071,349 B2 | 12/2011 | Dunn-Coleman et al. |
| 8,071,351 B2 | 12/2011 | Schnorr et al. |
| 8,080,398 B2 | 12/2011 | Holm et al. |
| 8,083,906 B2 | 12/2011 | Medoff |
| 8,092,647 B2 | 1/2012 | Akhtar et al. |
| 8,093,037 B2 | 1/2012 | Picataggio et al. |
| 8,097,442 B2 | 1/2012 | Hitchman et al. |
| 8,097,445 B2 | 1/2012 | Bower et al. |
| 8,101,024 B2 | 1/2012 | Wyman et al. |
| 8,101,393 B2 | 1/2012 | Gray et al. |
| 8,101,398 B2 | 1/2012 | St-Pierre et al. |
| 8,105,398 B2 | 1/2012 | Morgan |
| 8,114,655 B2 | 2/2012 | Dunn-Coleman et al. |
| 8,114,974 B2 | 2/2012 | Picataggio et al. |
| 8,119,385 B2 | 2/2012 | Mathur et al. |
| 8,133,711 B2 | 3/2012 | Dunn-Coleman et al. |
| 8,142,620 B2 | 3/2012 | Medoff |
| 8,143,050 B2 | 3/2012 | Yang et al. |
| 8,143,480 B2 | 3/2012 | Axtell et al. |
| 8,148,133 B2 | 4/2012 | Elias et al. |
| 8,148,579 B2 | 4/2012 | Bradin |
| 8,158,397 B2 | 4/2012 | Jones et al. |
| 8,168,038 B2 | 5/2012 | Medoff |
| 8,173,410 B2 | 5/2012 | Bott et al. |
| 8,178,336 B2 | 5/2012 | Derkx et al. |
| 8,187,860 B2 | 5/2012 | Franklin et al. |
| 8,192,968 B2 | 6/2012 | Edwards et al. |
| 8,202,709 B2 | 6/2012 | Tolan et al. |
| 8,202,831 B2 | 6/2012 | Lant et al. |
| 8,206,963 B2 | 6/2012 | Dicosimo et al. |
| 8,206,964 B2 | 6/2012 | DiCosimo et al. |
| 8,212,087 B2 | 7/2012 | Medoff |
| 8,216,815 B2 | 7/2012 | McDaniel et al. |
| 8,217,227 B2 | 7/2012 | Allen et al. |
| 8,222,010 B2 | 7/2012 | Franklin et al. |
| 8,227,236 B2 | 7/2012 | Picataggio et al. |
| 8,232,080 B2 | 7/2012 | Day et al. |
| 8,236,535 B2 | 8/2012 | Medoff et al. |
| 8,236,542 B2 | 8/2012 | Cascao-Pereira et al. |
| 8,236,546 B2 | 8/2012 | Goedegebuur et al. |
| 8,236,551 B2 | 8/2012 | Dhawan et al. |
| 8,241,461 B1 | 8/2012 | Dyer |
| 8,241,881 B2 | 8/2012 | Bradin |
| 8,247,203 B2 | 8/2012 | Foody et al. |
| 8,247,647 B2 | 8/2012 | Raab |
| 8,257,959 B2 | 9/2012 | Bell et al. |
| 8,263,368 B2 | 9/2012 | Svendsen et al. |
| 8,273,181 B2 | 9/2012 | Foody et al. |
| 8,273,559 B2 | 9/2012 | Geros |
| 8,278,079 B2 | 10/2012 | Dunn-Coleman et al. |
| 8,278,260 B2 | 10/2012 | Saint Victor |
| 8,283,150 B2 | 10/2012 | Adney et al. |
| 8,287,732 B2 | 10/2012 | Chen et al. |

(56) References Cited

U.S. PATENT DOCUMENTS

| | | |
|---|---|---|
| 8,288,144 B2 | 10/2012 | Glad et al. |
| 8,288,148 B2 | 10/2012 | Cervin et al. |
| 8,293,508 B2 | 10/2012 | Lantero et al. |
| 8,298,795 B2 | 10/2012 | Yang et al. |
| 8,298,799 B2 | 10/2012 | Bornscheuer et al. |
| 8,298,802 B2 | 10/2012 | Dunn-Coleman et al. |
| 8,304,219 B2 | 11/2012 | Levine |
| 8,309,328 B1 | 11/2012 | Dhawan et al. |
| 8,309,331 B2 | 11/2012 | Banerjee et al. |
| 8,317,975 B2 | 11/2012 | Amidon et al. |
| 8,318,461 B2 | 11/2012 | Tolan et al. |
| 8,323,947 B2 | 12/2012 | Yang et al. |
| 8,328,947 B2 | 12/2012 | Anand et al. |
| 8,334,430 B2 | 12/2012 | Allen et al. |
| 8,338,139 B2 | 12/2012 | Lail et al. |
| 8,343,747 B2 | 1/2013 | Burke et al. |
| 8,354,263 B2 | 1/2013 | Schnorr et al. |
| 8,357,523 B2 | 1/2013 | Postlethwaite et al. |
| 8,361,762 B2 | 1/2013 | Beck et al. |
| 8,361,767 B2 | 1/2013 | Dunn-Coleman et al. |
| 8,362,322 B2 | 1/2013 | Apuya et al. |
| 8,367,819 B2 | 2/2013 | Frost |
| 8,372,598 B2 | 2/2013 | Mucha |
| 8,377,659 B2 | 2/2013 | Goedegebuur et al. |
| 8,389,254 B2 | 3/2013 | Dicosimo et al. |
| 8,389,255 B2 | 3/2013 | Dicosimo et al. |
| 8,389,256 B2 | 3/2013 | Dicosimo et al. |
| 8,389,257 B2 | 3/2013 | Dicosimo et al. |
| 8,389,258 B2 | 3/2013 | DiCosimo et al. |
| 8,389,259 B2 | 3/2013 | DiCosimo et al. |
| 8,389,260 B2 | 3/2013 | DiCosimo et al. |
| 8,394,616 B2 | 3/2013 | DiCosimo et al. |
| 8,394,617 B2 | 3/2013 | DiCosimo et al. |
| 8,395,023 B2 | 3/2013 | Gilbertson et al. |
| 2001/0010825 A1 | 8/2001 | Shimizu et al. |
| 2001/0044138 A1 | 11/2001 | Watanabe et al. |
| 2002/0012980 A1 | 1/2002 | Sreenath |
| 2002/0045057 A1 | 4/2002 | Guritza |
| 2002/0142034 A1 | 10/2002 | Shimizu et al. |
| 2002/0156048 A1 | 10/2002 | Huppe et al. |
| 2002/0160469 A1 | 10/2002 | Ingram et al. |
| 2002/0164731 A1 | 11/2002 | Eroma et al. |
| 2002/0164774 A1 | 11/2002 | Fowler et al. |
| 2002/0193272 A1 | 12/2002 | Clarkson et al. |
| 2002/0195213 A1 | 12/2002 | Izumi et al. |
| 2003/0013172 A1 | 1/2003 | Gerendash |
| 2003/0022347 A1 | 1/2003 | Sjoholm et al. |
| 2003/0022807 A1 | 1/2003 | Wilting et al. |
| 2003/0032084 A1 | 2/2003 | Saville |
| 2003/0032148 A1 | 2/2003 | Watanabe et al. |
| 2003/0032162 A1 | 2/2003 | Schnorr et al. |
| 2003/0054500 A1 | 3/2003 | Ingram et al. |
| 2003/0054518 A1 | 3/2003 | Saloheimo et al. |
| 2003/0054539 A1 | 3/2003 | Schulein et al. |
| 2003/0082779 A1 | 5/2003 | Dunn-Coleman et al. |
| 2003/0087415 A1 | 5/2003 | Andersen et al. |
| 2003/0092097 A1 | 5/2003 | Andersen et al. |
| 2003/0097029 A1 | 5/2003 | Heikkila et al. |
| 2003/0113732 A1 | 6/2003 | Dunn-Coleman et al. |
| 2003/0113734 A1 | 6/2003 | Dunn-Coleman et al. |
| 2003/0113735 A1 | 6/2003 | Dunn-Coleman et al. |
| 2003/0114330 A1 | 6/2003 | Dunn-Coleman et al. |
| 2003/0119006 A1 | 6/2003 | Dunn-Coleman et al. |
| 2003/0125588 A1 | 7/2003 | Heikkila et al. |
| 2003/0180900 A1 | 9/2003 | Lantero |
| 2003/0203454 A1 | 10/2003 | Chotani et al. |
| 2003/0203466 A1 | 10/2003 | Kauppinen et al. |
| 2003/0211958 A1 | 11/2003 | Svendsen et al. |
| 2003/0216492 A1 | 11/2003 | Bowden et al. |
| 2003/0225005 A1 | 12/2003 | Gerson et al. |
| 2004/0053238 A1 | 3/2004 | Hseu et al. |
| 2004/0067569 A1 | 4/2004 | Rey et al. |
| 2004/0102619 A1 | 5/2004 | Dunn-Coleman et al. |
| 2004/0121436 A1 | 6/2004 | Blount |
| 2004/0157301 A1 | 8/2004 | Chotani et al. |
| 2004/0203134 A1 | 10/2004 | Pyntikov et al. |
| 2004/0210099 A1 | 10/2004 | Shiratori |
| 2004/0231661 A1 | 11/2004 | Griffin et al. |
| 2004/0259218 A1 | 12/2004 | Weimer et al. |
| 2004/0266642 A1 | 12/2004 | Schnorr et al. |
| 2005/0009166 A1 | 1/2005 | Andersen et al. |
| 2005/0037459 A1 | 2/2005 | Goedegebuur et al. |
| 2005/0054039 A1 | 3/2005 | Goedegebuur et al. |
| 2005/0070003 A1 | 3/2005 | Schulein et al. |
| 2005/0075497 A1 | 4/2005 | Utz et al. |
| 2005/0100996 A1 | 5/2005 | Lantero, Jr. et al. |
| 2005/0118130 A1 | 6/2005 | Utz et al. |
| 2005/0120915 A1 | 6/2005 | Bowden et al. |
| 2005/0125860 A1 | 6/2005 | Raab |
| 2005/0129643 A1 | 6/2005 | Lepilleur et al. |
| 2005/0148056 A1 | 7/2005 | Levine |
| 2005/0210548 A1 | 9/2005 | Yaver et al. |
| 2005/0214921 A1 | 9/2005 | Dunn-coleman et al. |
| 2005/0221369 A1 | 10/2005 | Dunn-Coleman et al. |
| 2005/0244878 A1 | 11/2005 | Dunn-Coleman et al. |
| 2005/0244934 A1 | 11/2005 | Foody et al. |
| 2005/0272836 A1 | 12/2005 | Yaginuma et al. |
| 2005/0277172 A1 | 12/2005 | Day et al. |
| 2006/0003433 A1 | 1/2006 | Steer et al. |
| 2006/0018862 A1 | 1/2006 | Chen et al. |
| 2006/0035353 A1 | 2/2006 | Zhao et al. |
| 2006/0046284 A1 | 3/2006 | Dunn-Coleman et al. |
| 2006/0057672 A1 | 3/2006 | Bower et al. |
| 2006/0068475 A1 | 3/2006 | Foody |
| 2006/0084156 A1 | 4/2006 | Lantero et al. |
| 2006/0089283 A1 | 4/2006 | Glad et al. |
| 2006/0104931 A1 | 5/2006 | Fukutome et al. |
| 2006/0110797 A1 | 5/2006 | Rey et al. |
| 2006/0135388 A1 | 6/2006 | Dunn-Coleman et al. |
| 2006/0141601 A1 | 6/2006 | Dunn-Coleman et al. |
| 2006/0154352 A1 | 7/2006 | Foody et al. |
| 2006/0154844 A1 | 7/2006 | Dunn-Coleman et al. |
| 2006/0165613 A1 | 7/2006 | Bjoernvad et al. |
| 2006/0166322 A1 | 7/2006 | Dunn-Coleman et al. |
| 2006/0182802 A1 | 8/2006 | Shimizu et al. |
| 2006/0188965 A1 | 8/2006 | Wyman et al. |
| 2006/0200878 A1 | 9/2006 | Lutfiyya et al. |
| 2006/0205042 A1 | 9/2006 | Aehle et al. |
| 2006/0210971 A1 | 9/2006 | Kerovuo et al. |
| 2006/0211101 A1 | 9/2006 | Chotani et al. |
| 2006/0235115 A1 | 10/2006 | Weimer et al. |
| 2006/0246563 A1 | 11/2006 | Eroma et al. |
| 2006/0255507 A1 | 11/2006 | Bowden et al. |
| 2006/0258554 A1 | 11/2006 | Dunn-Coleman et al. |
| 2006/0259995 A1 | 11/2006 | Cayouette et al. |
| 2006/0275241 A1 | 12/2006 | Padlo et al. |
| 2006/0281157 A1 | 12/2006 | Chotani et al. |
| 2007/0011775 A1 | 1/2007 | Allen et al. |
| 2007/0031918 A1 | 2/2007 | Dunson, Jr. et al. |
| 2007/0031919 A1 | 2/2007 | Dunson, Jr. et al. |
| 2007/0031953 A1 | 2/2007 | Dunson, Jr. et al. |
| 2007/0031954 A1 | 2/2007 | Mairal et al. |
| 2007/0036832 A1 | 2/2007 | Williams et al. |
| 2007/0037259 A1 | 2/2007 | Hennessey et al. |
| 2007/0059813 A1 | 3/2007 | Saville |
| 2007/0072185 A1 | 3/2007 | Schnorr et al. |
| 2007/0079944 A1 | 4/2007 | Amidon et al. |
| 2007/0083947 A1 | 4/2007 | Huang et al. |
| 2007/0083949 A1 | 4/2007 | Huang et al. |
| 2007/0083950 A1 | 4/2007 | Huang et al. |
| 2007/0083951 A1 | 4/2007 | Huang et al. |
| 2007/0083952 A1 | 4/2007 | Huang et al. |
| 2007/0087066 A1 | 4/2007 | Gerson et al. |
| 2007/0089184 A1 | 4/2007 | Huang et al. |
| 2007/0089185 A1 | 4/2007 | Huang et al. |
| 2007/0089186 A1 | 4/2007 | Huang et al. |
| 2007/0089187 A1 | 4/2007 | Huang et al. |
| 2007/0089188 A1 | 4/2007 | Huang et al. |
| 2007/0089189 A1 | 4/2007 | Huang et al. |
| 2007/0089190 A1 | 4/2007 | Huang et al. |
| 2007/0089191 A1 | 4/2007 | Huang et al. |
| 2007/0089192 A1 | 4/2007 | Huang et al. |
| 2007/0089193 A1 | 4/2007 | Huang et al. |
| 2007/0089194 A1 | 4/2007 | Huang et al. |

(56) References Cited

U.S. PATENT DOCUMENTS

| | | |
|---|---|---|
| 2007/0089195 A1 | 4/2007 | Huang et al. |
| 2007/0089196 A1 | 4/2007 | Huang et al. |
| 2007/0092934 A1 | 4/2007 | Jones et al. |
| 2007/0092935 A1 | 4/2007 | Jones et al. |
| 2007/0094748 A1 | 4/2007 | Huang et al. |
| 2007/0105112 A1 | 5/2007 | Hitchman et al. |
| 2007/0113301 A1 | 5/2007 | Huang et al. |
| 2007/0113302 A1 | 5/2007 | Huang et al. |
| 2007/0118917 A1 | 5/2007 | Huang et al. |
| 2007/0118918 A1 | 5/2007 | Huang et al. |
| 2007/0141660 A1 | 6/2007 | Chotani et al. |
| 2007/0141693 A1 | 6/2007 | Berg et al. |
| 2007/0148730 A1 | 6/2007 | Adney |
| 2007/0148751 A1 | 6/2007 | Griffin et al. |
| 2007/0149777 A1 | 6/2007 | Frost |
| 2007/0172916 A1 | 7/2007 | Jones et al. |
| 2007/0173431 A1 | 7/2007 | Day et al. |
| 2007/0175825 A1 | 8/2007 | Denney |
| 2007/0178569 A1 | 8/2007 | Leschine et al. |
| 2007/0192903 A1 | 8/2007 | Heck et al. |
| 2007/0199095 A1 | 8/2007 | Allen et al. |
| 2007/0199903 A1 | 8/2007 | Denney |
| 2007/0202566 A1 | 8/2007 | Bornscheuer et al. |
| 2007/0207530 A1 | 9/2007 | Dunn-Coleman et al. |
| 2007/0207939 A1 | 9/2007 | Fenyvesi et al. |
| 2007/0213249 A1 | 9/2007 | Dunn-Coleman et al. |
| 2007/0218541 A1 | 9/2007 | Denney et al. |
| 2007/0219521 A1 | 9/2007 | Hird et al. |
| 2007/0221552 A1 | 9/2007 | Denney |
| 2007/0227971 A1 | 10/2007 | Denney |
| 2007/0241306 A1 | 10/2007 | Wehner et al. |
| 2007/0254031 A1 | 11/2007 | Shimizu et al. |
| 2007/0298475 A1 | 12/2007 | Heald et al. |
| 2008/0009047 A1 | 1/2008 | Bell et al. |
| 2008/0020435 A1 | 1/2008 | Burke et al. |
| 2008/0029110 A1 | 2/2008 | Dube et al. |
| 2008/0034453 A1 | 2/2008 | Cheikh et al. |
| 2008/0056983 A1 | 3/2008 | Curren et al. |
| 2008/0064064 A1 | 3/2008 | Kensch et al. |
| 2008/0064906 A1 | 3/2008 | Foody et al. |
| 2008/0070291 A1 | 3/2008 | Lam et al. |
| 2008/0076152 A1 | 3/2008 | St-Pierre et al. |
| 2008/0076314 A1 | 3/2008 | Blanz et al. |
| 2008/0085520 A1 | 4/2008 | Nobles, Jr. et al. |
| 2008/0085536 A1 | 4/2008 | Nobles, Jr. et al. |
| 2008/0095889 A1 | 4/2008 | Dunn-Coleman et al. |
| 2008/0102502 A1 | 5/2008 | Foody et al. |
| 2008/0113413 A1 | 5/2008 | Nobles et al. |
| 2008/0138880 A1 | 6/2008 | Schnorr et al. |
| 2008/0145912 A1 | 6/2008 | Schulein et al. |
| 2008/0176282 A1 | 7/2008 | Dunn-Coleman et al. |
| 2008/0193981 A1 | 8/2008 | Fahrner et al. |
| 2008/0193992 A1 | 8/2008 | Levine |
| 2008/0201801 A1 | 8/2008 | Allen et al. |
| 2008/0202684 A1 | 8/2008 | Weimer et al. |
| 2008/0206836 A1 | 8/2008 | Andersen et al. |
| 2008/0227161 A1 | 9/2008 | Levie et al. |
| 2008/0227173 A1 | 9/2008 | Berg et al. |
| 2008/0227182 A1 | 9/2008 | Anderson et al. |
| 2008/0229456 A1 | 9/2008 | Huang et al. |
| 2008/0229657 A1 | 9/2008 | Senyk et al. |
| 2008/0233175 A1 | 9/2008 | Steer et al. |
| 2008/0241900 A1 | 10/2008 | Zhao et al. |
| 2008/0248160 A1 | 10/2008 | Steer et al. |
| 2008/0251374 A1 | 10/2008 | McManigal |
| 2008/0254080 A1 | 10/2008 | Glynson et al. |
| 2008/0261267 A1 | 10/2008 | Ferrer et al. |
| 2008/0274527 A1 | 11/2008 | Soerensen et al. |
| 2008/0292701 A1 | 11/2008 | Shimizu et al. |
| 2008/0292747 A1 | 11/2008 | Berg et al. |
| 2008/0293086 A1 | 11/2008 | Contag |
| 2008/0293114 A1 | 11/2008 | Foody et al. |
| 2008/0305531 A1 | 12/2008 | Lam et al. |
| 2008/0311640 A1 | 12/2008 | Cox et al. |
| 2009/0004714 A1 | 1/2009 | Norholm et al. |
| 2009/0004726 A1 | 1/2009 | Liu |
| 2009/0005532 A1 | 1/2009 | Frost |
| 2009/0013434 A1 | 1/2009 | Huang et al. |
| 2009/0017512 A1 | 1/2009 | May et al. |
| 2009/0025738 A1 | 1/2009 | Mua et al. |
| 2009/0025739 A1 | 1/2009 | Brinkley et al. |
| 2009/0035826 A1 | 2/2009 | Tolan et al. |
| 2009/0036648 A1 | 2/2009 | Dunn-Coleman et al. |
| 2009/0038023 A1 | 2/2009 | Weiner et al. |
| 2009/0042259 A1 | 2/2009 | Dale et al. |
| 2009/0042266 A1 | 2/2009 | Vehmaanpera et al. |
| 2009/0050134 A1 | 2/2009 | Friend et al. |
| 2009/0053777 A1 | 2/2009 | Hennessey et al. |
| 2009/0053800 A1 | 2/2009 | Friend et al. |
| 2009/0056201 A1 | 3/2009 | Morgan |
| 2009/0056707 A1 | 3/2009 | Foody et al. |
| 2009/0061490 A1 | 3/2009 | Edwards et al. |
| 2009/0068714 A1 | 3/2009 | Leschine et al. |
| 2009/0070898 A1 | 3/2009 | Allen et al. |
| 2009/0075336 A1 | 3/2009 | Goedegebuur et al. |
| 2009/0081762 A1 | 3/2009 | Adney et al. |
| 2009/0093028 A1 | 4/2009 | Doran Peterson et al. |
| 2009/0098266 A1 | 4/2009 | Briz et al. |
| 2009/0099079 A1 | 4/2009 | Emalfarb et al. |
| 2009/0136476 A1 | 5/2009 | Soerensen et al. |
| 2009/0137438 A1 | 5/2009 | Lepilleur et al. |
| 2009/0142848 A1 | 6/2009 | Wyman et al. |
| 2009/0155238 A1 | 6/2009 | Weiner et al. |
| 2009/0163397 A1 | 6/2009 | Goedegebuur et al. |
| 2009/0170174 A1 | 7/2009 | Czechowski et al. |
| 2009/0170181 A1 | 7/2009 | Dunn-Coleman et al. |
| 2009/0170747 A1 | 7/2009 | Andersen et al. |
| 2009/0172838 A1 | 7/2009 | Axtell et al. |
| 2009/0176292 A1 | 7/2009 | Dunn-Coleman et al. |
| 2009/0181126 A1 | 7/2009 | Wicking et al. |
| 2009/0181433 A1 | 7/2009 | Chotani et al. |
| 2009/0194243 A1 | 8/2009 | Akhtar et al. |
| 2009/0198046 A1 | 8/2009 | Fanselow et al. |
| 2009/0202675 A1 | 8/2009 | Derkx et al. |
| 2009/0203102 A1 | 8/2009 | Cervin et al. |
| 2009/0209009 A1 | 8/2009 | Tolan et al. |
| 2009/0217569 A1 | 9/2009 | Pastinen et al. |
| 2009/0220480 A1 | 9/2009 | Gray et al. |
| 2009/0221051 A1 | 9/2009 | Steer et al. |
| 2009/0224086 A1 | 9/2009 | Hata |
| 2009/0226979 A1 | 9/2009 | Retsina et al. |
| 2009/0233335 A1 | 9/2009 | Goedegebuur et al. |
| 2009/0234142 A1 | 9/2009 | Mascal |
| 2009/0235388 A1 | 9/2009 | Allen et al. |
| 2009/0247448 A1 | 10/2009 | Glad et al. |
| 2009/0258172 A1 | 10/2009 | Bowden et al. |
| 2009/0280105 A1 | 11/2009 | Gusakov et al. |
| 2009/0286294 A1 | 11/2009 | Blanchard et al. |
| 2009/0286295 A1 | 11/2009 | Medoff et al. |
| 2009/0297495 A1 | 12/2009 | Kerovuo et al. |
| 2009/0298149 A1 | 12/2009 | Wang et al. |
| 2009/0311752 A1 | 12/2009 | Bodie et al. |
| 2009/0312221 A1 | 12/2009 | Lant et al. |
| 2009/0312537 A1 | 12/2009 | Medoff |
| 2009/0317864 A1 | 12/2009 | Svendsen et al. |
| 2009/0318571 A1 | 12/2009 | Utz et al. |
| 2009/0324574 A1 | 12/2009 | Mathur et al. |
| 2009/0325254 A1 | 12/2009 | Zhao et al. |
| 2010/0003234 A1 | 1/2010 | Blum et al. |
| 2010/0003716 A1 | 1/2010 | Cervin et al. |
| 2010/0003733 A1 | 1/2010 | Foody et al. |
| 2010/0011456 A1 | 1/2010 | Mathur et al. |
| 2010/0021988 A1 | 1/2010 | Kerovuo et al. |
| 2010/0028966 A1 | 2/2010 | Blanchard et al. |
| 2010/0031398 A1 | 2/2010 | Lewis et al. |
| 2010/0035320 A1 | 2/2010 | Blanchard et al. |
| 2010/0041104 A1 | 2/2010 | Cascao-Pereira et al. |
| 2010/0048417 A1 | 2/2010 | Jones et al. |
| 2010/0048964 A1 | 2/2010 | Calabria et al. |
| 2010/0055747 A1 | 3/2010 | Kelemen et al. |
| 2010/0055753 A1 | 3/2010 | Geros |
| 2010/0056774 A1 | 3/2010 | Anand et al. |
| 2010/0068768 A1 | 3/2010 | Tolan et al. |
| 2010/0068790 A1 | 3/2010 | Bell et al. |

(56) References Cited

U.S. PATENT DOCUMENTS

| | | |
|---|---|---|
| 2010/0071259 A1 | 3/2010 | Hu et al. |
| 2010/0075404 A1 | 3/2010 | Templeton |
| 2010/0086978 A1 | 4/2010 | Beck et al. |
| 2010/0087687 A1 | 4/2010 | Medoff |
| 2010/0095390 A1 | 4/2010 | Weiner et al. |
| 2010/0099640 A1 | 4/2010 | Geuns et al. |
| 2010/0101605 A1 | 4/2010 | Saint Victor |
| 2010/0105114 A1 | 4/2010 | Blanchard et al. |
| 2010/0107342 A1 | 5/2010 | Schulein et al. |
| 2010/0108567 A1 | 5/2010 | Medoff |
| 2010/0112242 A1 | 5/2010 | Medoff |
| 2010/0113846 A1 | 5/2010 | McAuliffe et al. |
| 2010/0124583 A1 | 5/2010 | Medoff |
| 2010/0129835 A1 | 5/2010 | Bodie |
| 2010/0136113 A1 | 6/2010 | Steer et al. |
| 2010/0136661 A1 | 6/2010 | Leschine et al. |
| 2010/0137647 A1 | 6/2010 | Bradin |
| 2010/0143998 A1 | 6/2010 | Leschine et al. |
| 2010/0144584 A1 | 6/2010 | Saint Victor |
| 2010/0151546 A1 | 6/2010 | Leschine et al. |
| 2010/0151547 A1 | 6/2010 | Platz |
| 2010/0151551 A1 | 6/2010 | Leschine et al. |
| 2010/0159510 A1 | 6/2010 | Raab |
| 2010/0159553 A1 | 6/2010 | Bradin |
| 2010/0159566 A1 | 6/2010 | Leschine et al. |
| 2010/0160201 A1 | 6/2010 | Scheuing et al. |
| 2010/0167370 A1 | 7/2010 | Chotani et al. |
| 2010/0167371 A1 | 7/2010 | Chotani et al. |
| 2010/0179315 A1 | 7/2010 | Medoff |
| 2010/0184175 A1 | 7/2010 | Dunn-Coleman et al. |
| 2010/0184178 A1 | 7/2010 | Beck et al. |
| 2010/0189706 A1 | 7/2010 | Chang et al. |
| 2010/0196977 A1 | 8/2010 | Chotani et al. |
| 2010/0196978 A1 | 8/2010 | Wood et al. |
| 2010/0196981 A1 | 8/2010 | Aharon et al. |
| 2010/0199548 A1 | 8/2010 | del Cardayre et al. |
| 2010/0212091 A1 | 8/2010 | Schnorr et al. |
| 2010/0216200 A1 | 8/2010 | Leschine et al. |
| 2010/0221784 A1 | 9/2010 | Fujdala et al. |
| 2010/0221819 A1 | 9/2010 | Foody et al. |
| 2010/0223694 A1 | 9/2010 | Lutfiyya et al. |
| 2010/0240128 A1 | 9/2010 | Fillatti et al. |
| 2010/0263264 A1 | 10/2010 | Augier et al. |
| 2010/0267110 A1 | 10/2010 | Hitchman et al. |
| 2010/0268000 A1 | 10/2010 | Parekh et al. |
| 2010/0273214 A1 | 10/2010 | Holm et al. |
| 2010/0279354 A1 | 11/2010 | de Crecy |
| 2010/0279361 A1 | 11/2010 | South et al. |
| 2010/0285534 A1 | 11/2010 | South et al. |
| 2010/0287826 A1 | 11/2010 | Hoffman et al. |
| 2010/0291653 A1 | 11/2010 | Ness et al. |
| 2010/0297704 A1 | 11/2010 | Li |
| 2010/0297721 A1 | 11/2010 | Hogsett et al. |
| 2010/0298612 A1 | 11/2010 | Behrouzian et al. |
| 2010/0304420 A1 | 12/2010 | Gray |
| 2010/0304439 A1 | 12/2010 | Medoff |
| 2010/0304440 A1 | 12/2010 | Medoff |
| 2010/0312028 A1 | 12/2010 | Olson et al. |
| 2010/0317059 A1 | 12/2010 | Postlethwaite et al. |
| 2010/0317087 A1 | 12/2010 | St-Pierre et al. |
| 2010/0319862 A1 | 12/2010 | Rahman |
| 2010/0330633 A1 | 12/2010 | Walther et al. |
| 2011/0000125 A1 | 1/2011 | McDaniel et al. |
| 2011/0003341 A1 | 1/2011 | Nojiri et al. |
| 2011/0003345 A1 | 1/2011 | Nobles, Jr. et al. |
| 2011/0014672 A1 | 1/2011 | Chotani et al. |
| 2011/0016545 A1 | 1/2011 | Gray et al. |
| 2011/0020874 A1 | 1/2011 | Hata |
| 2011/0027346 A1 | 2/2011 | Weiner et al. |
| 2011/0027837 A1 | 2/2011 | Medoff |
| 2011/0028672 A1 | 2/2011 | Dahlman et al. |
| 2011/0033391 A1 | 2/2011 | Weiner et al. |
| 2011/0035838 A1 | 2/2011 | Lutfiyya et al. |
| 2011/0035839 A1 | 2/2011 | Lutfiyya et al. |
| 2011/0039308 A1 | 2/2011 | Slupska et al. |
| 2011/0039309 A1 | 2/2011 | Conner et al. |
| 2011/0039317 A1 | 2/2011 | Medoff |
| 2011/0039318 A1 | 2/2011 | Lehr |
| 2011/0039320 A1 | 2/2011 | Li et al. |
| 2011/0040058 A1 | 2/2011 | McAuliffe et al. |
| 2011/0045544 A1 | 2/2011 | Vehmaanpera et al. |
| 2011/0046422 A1 | 2/2011 | McAuliffe et al. |
| 2011/0053245 A1 | 3/2011 | Weiner et al. |
| 2011/0061666 A1 | 3/2011 | Dube et al. |
| 2011/0065910 A1 | 3/2011 | Medoff |
| 2011/0076743 A1 | 3/2011 | Beck et al. |
| 2011/0081335 A1 | 4/2011 | Medoff |
| 2011/0081336 A1 | 4/2011 | Medoff |
| 2011/0081412 A1 | 4/2011 | Shimizu et al. |
| 2011/0081697 A1 | 4/2011 | Liu |
| 2011/0086408 A1 | 4/2011 | Power et al. |
| 2011/0086410 A1 | 4/2011 | Dunn-Coleman et al. |
| 2011/0091940 A1 | 4/2011 | Atalla |
| 2011/0091950 A1 | 4/2011 | Hansen et al. |
| 2011/0093965 A1 | 4/2011 | O'Donoghue et al. |
| 2011/0095111 A1 | 4/2011 | Briz et al. |
| 2011/0097786 A1 | 4/2011 | Howard et al. |
| 2011/0100359 A1 | 5/2011 | North |
| 2011/0111456 A1 | 5/2011 | Medoff |
| 2011/0117067 A1 | 5/2011 | Esteghlalian et al. |
| 2011/0117619 A1 | 5/2011 | Hansen et al. |
| 2011/0124058 A1 | 5/2011 | Baidyaroy et al. |
| 2011/0124074 A1 | 5/2011 | Den Haan et al. |
| 2011/0125118 A1 | 5/2011 | Lynch |
| 2011/0129880 A1 | 6/2011 | Conners et al. |
| 2011/0129881 A1 | 6/2011 | Yang et al. |
| 2011/0129886 A1 | 6/2011 | Howard et al. |
| 2011/0129887 A1 | 6/2011 | Contag et al. |
| 2011/0130488 A1 | 6/2011 | Yoshino et al. |
| 2011/0136174 A1 | 6/2011 | Kosugi et al. |
| 2011/0136196 A1 | 6/2011 | Elias et al. |
| 2011/0136907 A1 | 6/2011 | DiCosimo et al. |
| 2011/0136908 A1 | 6/2011 | DiCosimo et al. |
| 2011/0138502 A1 | 6/2011 | Raab |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0143398 A1 | 6/2011 | Howard et al. |
| 2011/0144241 A1 | 6/2011 | Yoshino et al. |
| 2011/0146138 A1 | 6/2011 | Berry et al. |
| 2011/0146142 A1 | 6/2011 | Lee et al. |
| 2011/0150857 A1 | 6/2011 | Dicosimo et al. |
| 2011/0152368 A1 | 6/2011 | DiCosimo et al. |
| 2011/0152369 A1 | 6/2011 | DiCosimo et al. |
| 2011/0152370 A1 | 6/2011 | DiCosimo et al. |
| 2011/0152812 A1 | 6/2011 | Hird et al. |
| 2011/0155559 A1 | 6/2011 | Medoff |
| 2011/0159544 A1 | 6/2011 | Puranen et al. |
| 2011/0165660 A1 | 7/2011 | Picataggio et al. |
| 2011/0165661 A1 | 7/2011 | Picataggio et al. |
| 2011/0171705 A1 | 7/2011 | Kotlar et al. |
| 2011/0171709 A1 | 7/2011 | Bardsley |
| 2011/0177561 A1 | 7/2011 | Goedegebuur et al. |
| 2011/0177565 A1 | 7/2011 | Cho et al. |
| 2011/0177573 A1 | 7/2011 | All et al. |
| 2011/0178261 A1 | 7/2011 | Feher et al. |
| 2011/0183379 A1 | 7/2011 | Ladisch et al. |
| 2011/0183396 A1 | 7/2011 | Noda et al. |
| 2011/0185456 A1 | 7/2011 | Cheikh et al. |
| 2011/0190488 A1 | 8/2011 | Wicks |
| 2011/0195481 A1 | 8/2011 | Svendsen et al. |
| 2011/0201093 A1 | 8/2011 | Czechowski et al. |
| 2011/0207192 A1 | 8/2011 | Pigeau et al. |
| 2011/0212499 A1 | 9/2011 | Ladisch et al. |
| 2011/0212505 A1 | 9/2011 | Dunn-Coleman et al. |
| 2011/0224416 A1 | 9/2011 | Picataggio et al. |
| 2011/0229956 A1 | 9/2011 | Day et al. |
| 2011/0229959 A1 | 9/2011 | Picataggio et al. |
| 2011/0232160 A1 | 9/2011 | Siskin et al. |
| 2011/0232161 A1 | 9/2011 | Siskin et al. |
| 2011/0232162 A1 | 9/2011 | Siskin et al. |
| 2011/0232163 A1 | 9/2011 | Siskin et al. |
| 2011/0232164 A1 | 9/2011 | Siskin et al. |

(56) References Cited

U.S. PATENT DOCUMENTS

| | | |
|---|---|---|
| 2011/0233042 A1 | 9/2011 | Siskin et al. |
| 2011/0236335 A1 | 9/2011 | Dicosimo et al. |
| 2011/0236336 A1 | 9/2011 | DiCosimo et al. |
| 2011/0236337 A1 | 9/2011 | Dicosimo et al. |
| 2011/0236338 A1 | 9/2011 | Dicosimo et al. |
| 2011/0236339 A1 | 9/2011 | DiCosimo et al. |
| 2011/0237769 A1 | 9/2011 | Feher et al. |
| 2011/0239333 A1 | 9/2011 | Yaver et al. |
| 2011/0250635 A1 | 10/2011 | Paz Briz et al. |
| 2011/0250638 A1 | 10/2011 | Sjoede et al. |
| 2011/0250646 A1 | 10/2011 | Bazzana et al. |
| 2011/0250667 A1 | 10/2011 | Elias et al. |
| 2011/0250674 A1 | 10/2011 | Andersen et al. |
| 2011/0251377 A1 | 10/2011 | Rahman et al. |
| 2011/0262984 A1 | 10/2011 | Nguyen |
| 2011/0262985 A1 | 10/2011 | Medoff |
| 2011/0268858 A1 | 11/2011 | Heald et al. |
| 2011/0269201 A1 | 11/2011 | Gray et al. |
| 2011/0271875 A1 | 11/2011 | Ahmed et al. |
| 2011/0275118 A1 | 11/2011 | De Crecy |
| 2011/0275130 A1 | 11/2011 | Pronk et al. |
| 2011/0294164 A1 | 12/2011 | Goedegebuur et al. |
| 2011/0294165 A1 | 12/2011 | Goedegebuur et al. |
| 2011/0294181 A1 | 12/2011 | Weydahl |
| 2011/0296543 A1 | 12/2011 | Chang et al. |
| 2011/0296555 A1 | 12/2011 | Ivashuta et al. |
| 2011/0300585 A1 | 12/2011 | Banerjee et al. |
| 2011/0300586 A1 | 12/2011 | Liu et al. |
| 2011/0306083 A1 | 12/2011 | Mucha |
| 2011/0306100 A1 | 12/2011 | De Crecy |
| 2011/0306101 A1 | 12/2011 | De Crecy |
| 2011/0306117 A1 | 12/2011 | Lam et al. |
| 2011/0312048 A1 | 12/2011 | Fanselow et al. |
| 2011/0312055 A1 | 12/2011 | Weydahl |
| 2011/0312058 A1 | 12/2011 | Sibbesen et al. |
| 2011/0314726 A1 | 12/2011 | Jameel et al. |
| 2011/0315154 A1 | 12/2011 | Mua et al. |
| 2011/0318796 A1 | 12/2011 | Walther |
| 2011/0318798 A1 | 12/2011 | Walther et al. |
| 2011/0319849 A1 | 12/2011 | Collias et al. |
| 2012/0003701 A1 | 1/2012 | Brevnova et al. |
| 2012/0003703 A1 | 1/2012 | Mitchell et al. |
| 2012/0003704 A1 | 1/2012 | Medoff |
| 2012/0005949 A1 | 1/2012 | Stevens et al. |
| 2012/0006320 A1 | 1/2012 | Nguyen |
| 2012/0009631 A1 | 1/2012 | Yang et al. |
| 2012/0009634 A1 | 1/2012 | Burke et al. |
| 2012/0009640 A1 | 1/2012 | Behrouzian et al. |
| 2012/0010436 A1 | 1/2012 | Lee et al. |
| 2012/0010437 A1 | 1/2012 | Jevtic et al. |
| 2012/0010438 A1 | 1/2012 | Lee et al. |
| 2012/0010439 A1 | 1/2012 | Jevtic et al. |
| 2012/0010440 A1 | 1/2012 | Sarager et al. |
| 2012/0010443 A1 | 1/2012 | Jevtic et al. |
| 2012/0010444 A1 | 1/2012 | Horton et al. |
| 2012/0010445 A1 | 1/2012 | Johnston et al. |
| 2012/0010446 A1 | 1/2012 | Warner et al. |
| 2012/0010447 A1 | 1/2012 | Warner et al. |
| 2012/0010448 A1 | 1/2012 | Sarager et al. |
| 2012/0015408 A1 | 1/2012 | Baidyaroy et al. |
| 2012/0015422 A1 | 1/2012 | Huang et al. |
| 2012/0021092 A1 | 1/2012 | Sibbesen et al. |
| 2012/0021490 A1 | 1/2012 | Steer et al. |
| 2012/0028306 A1 | 2/2012 | Sibbesen et al. |
| 2012/0028325 A1 | 2/2012 | Herring et al. |
| 2012/0029247 A1 | 2/2012 | Holbrey et al. |
| 2012/0030838 A1 | 2/2012 | Gusakov et al. |
| 2012/0035400 A1 | 2/2012 | Johnston et al. |
| 2012/0036599 A1 | 2/2012 | Gusakov et al. |
| 2012/0036768 A1 | 2/2012 | Phillips et al. |
| 2012/0036769 A1 | 2/2012 | Johnston et al. |
| 2012/0040409 A1 | 2/2012 | Hau et al. |
| 2012/0040435 A1 | 2/2012 | Aehle et al. |
| 2012/0041075 A1 | 2/2012 | Johnston et al. |
| 2012/0045811 A1 | 2/2012 | Dunn-Coleman et al. |
| 2012/0045812 A1 | 2/2012 | Bergsma et al. |
| 2012/0046501 A1 | 2/2012 | Warner et al. |
| 2012/0052534 A1 | 3/2012 | Harlick et al. |
| 2012/0059197 A1 | 3/2012 | Jevtic et al. |
| 2012/0064579 A1 | 3/2012 | Kelley et al. |
| 2012/0064592 A1 | 3/2012 | O'Mullan et al. |
| 2012/0064609 A1 | 3/2012 | Clement et al. |
| 2012/0066781 A1 | 3/2012 | Weiner et al. |
| 2012/0077216 A1 | 3/2012 | Zhang et al. |
| 2012/0077247 A1 | 3/2012 | Medoff |
| 2012/0079665 A1 | 4/2012 | Schnorr et al. |
| 2012/0083019 A1 | 4/2012 | Baidyaroy et al. |
| 2012/0094340 A1 | 4/2012 | Morgan |
| 2012/0094343 A1 | 4/2012 | Hogsett et al. |
| 2012/0094355 A1 | 4/2012 | Medoff |
| 2012/0094358 A1 | 4/2012 | Medoff |
| 2012/0097194 A1 | 4/2012 | McDaniel et al. |
| 2012/0100045 A1 | 4/2012 | Beldring et al. |
| 2012/0100587 A1 | 4/2012 | Dunn-Coleman et al. |
| 2012/0101250 A1 | 4/2012 | Sakuma et al. |
| 2012/0107880 A1 | 5/2012 | Baidyaroy et al. |
| 2012/0107881 A1 | 5/2012 | Dhawan et al. |
| 2012/0107887 A1 | 5/2012 | Chheda et al. |
| 2012/0107888 A1 | 5/2012 | Schmalisch et al. |
| 2012/0107892 A1 | 5/2012 | Agbogbo et al. |
| 2012/0108798 A1 | 5/2012 | Wenger et al. |
| 2012/0111321 A1 | 5/2012 | Nguyen et al. |
| 2012/0115192 A1 | 5/2012 | Lali et al. |
| 2012/0129229 A1 | 5/2012 | McBride et al. |
| 2012/0129696 A1 | 5/2012 | Kohle et al. |
| 2012/0135489 A1 | 5/2012 | Weydahl |
| 2012/0135499 A1 | 5/2012 | Bower et al. |
| 2012/0135500 A1 | 5/2012 | Aehle et al. |
| 2012/0142046 A1 | 6/2012 | McBride et al. |
| 2012/0142065 A1 | 6/2012 | Medoff |
| 2012/0142068 A1 | 6/2012 | Medoff |
| 2012/0142886 A1 | 6/2012 | Frost |
| 2012/0146468 A1 | 6/2012 | Uehira et al. |
| 2012/0149065 A1 | 6/2012 | DaCunha et al. |
| 2012/0149077 A1 | 6/2012 | Shaw, IV et al. |
| 2012/0149949 A1 | 6/2012 | Weiner et al. |
| 2012/0151827 A1 | 6/2012 | Powell et al. |
| 2012/0156155 A1 | 6/2012 | Dicosimo et al. |
| 2012/0156156 A1 | 6/2012 | Dicosimo et al. |
| 2012/0156157 A1 | 6/2012 | DiCosimo et al. |
| 2012/0156158 A1 | 6/2012 | DiCosimo et al. |
| 2012/0156159 A1 | 6/2012 | DiCosimo et al. |
| 2012/0156160 A1 | 6/2012 | DiCosimo et al. |
| 2012/0156161 A1 | 6/2012 | DiCosimo et al. |
| 2012/0156162 A1 | 6/2012 | Dicosimo et al. |
| 2012/0156741 A1 | 6/2012 | Chheda et al. |
| 2012/0156754 A1 | 6/2012 | Dhawan et al. |
| 2012/0157721 A1 | 6/2012 | Weiner et al. |
| 2012/0157725 A1 | 6/2012 | McAuliffe |
| 2012/0159839 A1 | 6/2012 | Koskinen et al. |
| 2012/0159840 A1 | 6/2012 | Koskinen et al. |
| 2012/0164696 A1 | 6/2012 | Yang et al. |
| 2012/0164709 A1 | 6/2012 | Yang et al. |
| 2012/0165517 A1 | 6/2012 | Uehira et al. |
| 2012/0165562 A1 | 6/2012 | Hattendorf et al. |
| 2012/0171732 A1 | 7/2012 | Norholm et al. |
| 2012/0178975 A1 | 7/2012 | Weiner et al. |
| 2012/0184007 A1 | 7/2012 | Picataggio et al. |
| 2012/0184020 A1 | 7/2012 | Picataggio et al. |
| 2012/0190054 A1 | 7/2012 | Malten et al. |
| 2012/0190076 A1 | 7/2012 | Clark et al. |
| 2012/0190840 A1 | 7/2012 | Weydahl |
| 2012/0196338 A1 | 8/2012 | Blanchard et al. |
| 2012/0199298 A1 | 8/2012 | Dyer |
| 2012/0199299 A1 | 8/2012 | Dyer |
| 2012/0208235 A1 | 8/2012 | Zhang et al. |
| 2012/0209034 A1 | 8/2012 | Zhou et al. |
| 2012/0210467 A1 | 8/2012 | Barton et al. |
| 2012/0211184 A1 | 8/2012 | Jemaa et al. |
| 2012/0214209 A1 | 8/2012 | Chotani et al. |
| 2012/0216705 A1 | 8/2012 | Rogers et al. |
| 2012/0220513 A1 | 8/2012 | Allesen-Holm et al. |
| 2012/0231510 A1 | 9/2012 | Rao et al. |
| 2012/0237983 A1 | 9/2012 | Harlick |

(56) References Cited

U.S. PATENT DOCUMENTS

| | | |
|---|---|---|
| 2012/0237984 A1 | 9/2012 | Medoff |
| 2012/0238785 A1 | 9/2012 | Zhou et al. |
| 2012/0245336 A1 | 9/2012 | Daly et al. |
| 2012/0252085 A1 | 10/2012 | Edwards et al. |
| 2012/0264107 A1 | 10/2012 | Contag |
| 2012/0266328 A1 | 10/2012 | Gray et al. |
| 2012/0266329 A1 | 10/2012 | Mathur et al. |
| 2012/0270270 A1 | 10/2012 | Goedegebuur et al. |
| 2012/0270278 A1 | 10/2012 | Dhawan et al. |
| 2012/0270289 A1 | 10/2012 | Jeffries et al. |
| 2012/0270298 A1 | 10/2012 | Day et al. |
| 2012/0273338 A1 | 11/2012 | Lee et al. |
| 2012/0273339 A1 | 11/2012 | Lee et al. |
| 2012/0276594 A1 | 11/2012 | Voladri et al. |
| 2012/0276595 A1 | 11/2012 | Cascao-Pereira et al. |
| 2012/0277480 A1 | 11/2012 | Lee et al. |
| 2012/0277481 A1 | 11/2012 | Warner et al. |
| 2012/0277482 A1 | 11/2012 | Lee et al. |
| 2012/0277483 A1 | 11/2012 | Horton et al. |
| 2012/0277485 A1 | 11/2012 | Lee et al. |
| 2012/0277486 A1 | 11/2012 | Warner et al. |
| 2012/0277487 A1 | 11/2012 | Lee et al. |
| 2012/0277488 A1 | 11/2012 | Horton et al. |
| 2012/0277489 A1 | 11/2012 | Scates et al. |
| 2012/0277490 A1 | 11/2012 | Lee et al. |
| 2012/0277491 A1 | 11/2012 | Warner et al. |
| 2012/0282239 A1 | 11/2012 | Kensch |
| 2012/0282664 A1 | 11/2012 | Kondo et al. |
| 2012/0282666 A1 | 11/2012 | Noda et al. |
| 2012/0283164 A1 | 11/2012 | Svendsen et al. |
| 2012/0283493 A1 | 11/2012 | Olson et al. |
| 2012/0289450 A1 | 11/2012 | Andersen et al. |
| 2012/0289607 A1 | 11/2012 | Xiong et al. |
| 2012/0291160 A1 | 11/2012 | Raab |
| 2012/0301944 A1 | 11/2012 | Dunn-Coleman et al. |
| 2012/0309060 A1 | 12/2012 | Medoff |
| 2012/0315683 A1 | 12/2012 | Mosier et al. |
| 2012/0316330 A1 | 12/2012 | Zhu et al. |
| 2012/0316376 A1 | 12/2012 | Medoff |
| 2012/0321581 A1 | 12/2012 | DiCosimo et al. |
| 2012/0322078 A1 | 12/2012 | Mcbride et al. |
| 2012/0322117 A1 | 12/2012 | Anton et al. |
| 2012/0322121 A1 | 12/2012 | Mosier et al. |
| 2012/0323049 A1 | 12/2012 | Lee et al. |
| 2012/0323050 A1 | 12/2012 | Lee et al. |
| 2012/0325203 A1 | 12/2012 | Griffin et al. |
| 2012/0329096 A1 | 12/2012 | Foody et al. |
| 2012/0329100 A1 | 12/2012 | Uraki et al. |
| 2012/0329104 A1 | 12/2012 | Kim et al. |
| 2013/0011886 A1 | 1/2013 | Tolan et al. |
| 2013/0011887 A1 | 1/2013 | Dayton et al. |
| 2013/0011895 A1 | 1/2013 | Medoff et al. |
| 2013/0012424 A1 | 1/2013 | Glad et al. |
| 2013/0014293 A1 | 1/2013 | Lin et al. |
| 2013/0023608 A1 | 1/2013 | Kellett et al. |
| 2013/0029382 A1 | 1/2013 | Steffens et al. |
| 2013/0030215 A1 | 1/2013 | Bui et al. |
| 2013/0032466 A1 | 2/2013 | Lee et al. |
| 2013/0034888 A1 | 2/2013 | Aurora et al. |
| 2013/0034891 A1 | 2/2013 | Fanselow et al. |
| 2013/0035516 A1 | 2/2013 | Orosco et al. |
| 2013/0035518 A1 | 2/2013 | Lee et al. |
| 2013/0035519 A1 | 2/2013 | Lee et al. |
| 2013/0035520 A1 | 2/2013 | Jevtic et al. |
| 2013/0035521 A1 | 2/2013 | Orosco et al. |
| 2013/0035522 A1 | 2/2013 | Orosco et al. |
| 2013/0035523 A1 | 2/2013 | Lee et al. |
| 2013/0035524 A1 | 2/2013 | Orosco et al. |
| 2013/0035525 A1 | 2/2013 | Johnston et al. |
| 2013/0040352 A1 | 2/2013 | McDaniel et al. |
| 2013/0045891 A1 | 2/2013 | Beck et al. |
| 2013/0046032 A1 | 2/2013 | Scates et al. |
| 2013/0046119 A1 | 2/2013 | Scates et al. |
| 2013/0046120 A1 | 2/2013 | Zink et al. |
| 2013/0052693 A1 | 2/2013 | Baidyaroy et al. |
| 2013/0052694 A1 | 2/2013 | Montalibet et al. |
| 2013/0052698 A1 | 2/2013 | Yang et al. |
| 2013/0052713 A1 | 2/2013 | Yang et al. |
| 2013/0060070 A1 | 3/2013 | Huber et al. |
| 2013/0065270 A1 | 3/2013 | Bell et al. |

OTHER PUBLICATIONS

Arvelakis et al. Simultaneous Thermal Analysis (STA) on Ash from High-Alkali Biomass., Energy & Fuels (2004), vol. 18, pp. 1066-1076.*
Tschirner et al. Recycling of Chemical Pulp From Wheat Straw and Corn Stover., BioResources (2007), vol. 2(4), pp. 536-543.*
Hu et al. The enhancement of enzymatic hydrolysis of lignocellulosic substrates by the addition of accessory enzymes such as xylanase: is it an additive or synergistic effect?, Biotechnology for Biofuels (2011), vol. 4:36, pp. 1 to 13.*
Kinnarinen et al. Influence of enzyme loading on enzymatic hydrolysis of cardboard waste and size distribution of the resulting fiber residue., Bioresource Technology (Epub Mar. 3, 2014), vol. 159, p. 136-142.*
Robertson (2012), Food Packaging. Principles and Practice, Third Edition, CRC Press, p. 258.*
Ioelovich., Waste Paper as Promising Feedstock for Production of Biofuel., Journal of Scientific Research & Reports, Journal of Scientific Research & Reports (Feb. 22, 2014), vol. 3(7), pp. 905-916.*
Chemicool (last viewed on Dec. 1, 2016).*
Zhang, Yi-Heng Percival, and Lee R. Lynd. "Toward an aggregated understanding of enzymatic hydrolysis of cellulose: noncomplexed cellulase systems." Biotechnology and bioengineering 88.7 (2004): 797-824.
Fan, L. T., Yong-Hyun Lee, and David H. Beardmore. "Mechanism of the enzymatic hydrolysis of cellulose: effects of major structural features of cellulose on enzymatic hydrolysis." Biotechnology and Bioengineering 22.1 (1980): 177-199.
Mandels, Mary, Lloyd Hontz, and John Nystrom. "Enzymatic hydrolysis of waste cellulose." Biotechnology and Bioengineering 16.11 (2004): 1471-1493.
Philippidis, George P., Tammy K. Smith, and Charles E. Wyman. "Study of the enzymatic hydrolysis of cellulose for production of fuel ethanol by the simultaneous saccharification and fermentation process." Biotechnology and bioengineering 41.9 (1993): 846-853.
Pääkkö, M., et al. "Enzymatic hydrolysis combined with mechanical shearing and high-pressure homogenization for nanoscale cellulose fibrils and strong gels." Biomacromolecules 8.6 (2007): 1934-1941.
Yang, Bin, and Charles E. Wyman. "BSA treatment to enhance enzymatic hydrolysis of cellulose in lignin containing substrates." Biotechnology and Bioengineering 94.4 (2006): 611-617.
Sun, Ye, and Jiayang Cheng. "Hydrolysis of lignocellulosic materials for ethanol production: a review." Bioresource technology 83.1 (2002): 1-11.
Saddler, J. N., et al. "Enzymatic hydrolysis of cellulose and various pretreated wood fractions." Biotechnology and bioengineering 24.6 (1982): 1389-1402.
Khodaverdi, Mandi, et al. "Kinetic modeling of rapid enzymatic hydrolysis of crystalline cellulose after pretreatment by NMMO." Journal of industrial microbiology & biotechnology (2012): 1-10.
Obama, Patrick, et al. "Combination of enzymatic hydrolysis and ethanol organosolv pretreatments: Effect on lignin structures, delignification yields and cellulose-to-glucose conversion." Bioresource Technology (2012).
Wiman, Magnus, et al. "Cellulose accessibility determines the rate of enzymatic hydrolysis of steam-pretreated spruce." Bioresource Technology (2012).
Elliston, Adam, et al. "High concentrations of cellulosic ethanol achieved by fed batch semi simultaneous saccharification and fermentation of waste-paper." Bioresource Technology (2013).
Kinnarinen, Teemu, et al. "Effect of mixing on enzymatic hydrolysis of cardboard waste: Saccharification yield and subsequent separation of the solid residue using a pressure filter." Bioresource technology (2012).

(56) References Cited

OTHER PUBLICATIONS

Wang, Lei, Richard Templer, and Richard J. Murphy. "High-solids loading enzymatic hydrolysis of waste papers for biofuel production." Applied Energy (2012).
Li, Sujing, Xiaonan Zhang, and John M. Andresen. "Production of fermentable sugars from enzymatic hydrolysis of pretreated municipal solid waste after autoclave process." Fuel 92.1 (2012): 84-88.
Dubey, Alok Kumar, et al. "Bioethanol production from waste paper acid pretreated hydrolyzate with xylose fermenting< i> Pichia stipitis</i>." Carbohydrate Polymers (2012).
Kinnarinen, Teemu, et al. "Solid-liquid separation of hydrolysates obtained from enzymatic hydrolysis of cardboard waste." Industrial Crops and Products 38 (2012): 72-80.
Kang, Li. Bioconversion of Pulp and Paper Mills Sludge and Prehydrolysate Stream into Ethanol and Cellulase Enzyme. Diss. Auburn University, 2011.
Das, Arpan, et al. "Production of Cellulolytic Enzymes by Aspergillus fumigatus ABK9 in Wheat Bran-Rice Straw Mixed Substrate and Use of Cocktail Enzymes for Deinking of Waste Office Paper Pulp." Bioresource technology (2012).
Chen, Hui, et al. "Enzymatic Hydrolysis of Recovered Office Printing Paper with Low Enzyme Dosages to Produce Fermentable Sugars." Applied biochemistry and biotechnology (2012): 1-16.
Yan, Shoubao, et al. "Fed batch enzymatic saccharification of food waste improves the sugar concentration in the hydrolysates and eventually the ethanol fermentation by Saccharomyces cerevisiae H058." Brazilian Archives of Biology and Technology 55.2 (2012): 183-192.
Arora, Anju, et al. "Effect of Formic Acid and Furfural on the Enzymatic Hydrolysis of Cellulose Powder and Dilute Acid-Pretreated Poplar Hydrolysates." ACS Sustainable Chemistry & Engineering 1.1 (2012): 23-28.
Wang, Lei, et al. "Technology performance and economic feasibility of bioethanol production from various waste papers." Energy & Environmental Science 5.2 (2012): 5717-5730.
Vazana, Yael, et al. "Designer Cellulosomes for Enhanced Hydrolysis of Cellulosic Substrates." Cellulases (2012): 429.
Van Dyk, J. S., and B. I. Pletschke. "A review of lignocellulose bioconversion using enzymatic hydrolysis and synergistic cooperation between enzymes—Factors affecting enzymes, conversion and synergy." Biotechnology Advances (2012).
Menind, A., et al. "Pretreatment and usage of pulp and paper industry residues for fuels production and their energetic potential." International Scientific Conference Biosystems Engineering, Tartu, Estonia, May 10-11, 2012.. vol. 10. No. Special Issue I. Estonian Research Institute of Agriculture, 2012.
Han, Lirong, et al. "Alkali pretreated of wheat straw and its enzymatic hydrolysis." Brazilian Journal of Microbiology 43.1 (2012): 53-61.
Holm, Jana, et al. "Pretreatment of fibre sludge in ionic liquids followed by enzyme and acid catalysed hydrolysis." Catalysis Today (2012).
Van Heiningen, Adriaan. "Converting a kraft pulp mill into an integrated forest products biorefinery." Annual Meeting—Pulp and Paper Technical Association of Canada. vol. 92. No. C. Pulp and Paper Technical Association of Canada; 1999, 2006.
Zhu, J. Y., and X. J. Pan. "Woody biomass pretreatment for cellulosic ethanol production: technology and energy consumption evaluation." Bioresource technology 101.13 (2010): 4992-5002.
Pérez, J., et al. "Biodegradation and biological treatments of cellulose, hemicellulose and lignin: an overview." International Microbiology 5.2 (2002): 53-63.
Kadam, Kiran L., Chim Y. Chin, and Lawrence W. Brown. "Flexible biorefinery for producing fermentation sugars, lignin and pulp from corn stover." Journal of industrial microbiology & biotechnology 35.5 (2008): 331-341.
Kuhad, Ramesh Chander, and Ajay Singh. "Lignocellulose biotechnology: current and future prospects." Critical Reviews in Biotechnology 13.2 (1993): 151-172.
Lawford, Hugh G., and Joyce D. Rousseau. "Production of ethanol from pulp mill hardwood and softwood spent sulfite liquors by genetically engineered E. coli." Applied biochemistry and biotechnology 39.1 (1993): 667-685.
Burchhardt, G., and L. O. Ingram. "Conversion of xylan to ethanol by ethanologenic strains of Escherichia coli and Klebsiella oxytoca." Applied and environmental microbiology 58.4 (1992): 1128-1133.
Zhu, J. Y., Ronald Sabo, and Xiaolin Luo. "Integrated production of nano-fibrillated cellulose and cellulosic biofuel (ethanol) by enzymatic fractionation of wood fibers." Green Chemistry 13.5 (2011): 1339-1344.
Ichiura, Hideaki, Takuhiro Nakatani, and Yoshito Ohtani. "Separation of pulp and inorganic materials from paper sludge using ionic liquid and centrifugation." Chemical Engineering Journal 173.1 (2011): 129-134.
López-Contreras, Ana M., et al. "Utilisation of saccharides in extruded domestic organic waste by Clostridium acetobutylicum ATCC 824 for production of acetone, butanol and ethanol." Applied microbiology and biotechnology 54.2 (2000): 162-167.
Zhang, Xiao, et al. "High consistency enzymatic hydrolysis of hardwood substrates." Bioresource technology 100.23 (2009): 5890-5897.
Kirk, T. Kent, T. W. Jeffries, and George F. Leatham. "Biotechnology: applications and implications for the pulp and paper industry." Tappi J 66.5 (1983): 45-51.
Yamashita, Yuya, et al. "Ethanol production from paper sludge by immobilized Zymomonas mobilis." Biochemical Engineering Journal 42.3 (2008): 314-319.
Lee, Sang-Mok, Jianqiang Lin, and Yoon-Mo Koo. "Hydrolysis of Paper Sludge Using Mixed Cellulase System: Enzymtic Hydrolysis of Paper Sludge." ACS Symposium Series. vol. 830. Washington, DC; American Chemical Society; 1999, 2002.
Kang, Li, et al. "Enhanced Ethanol Production from De-Ashed Paper Sludge by Simultaneous Saccharification and Fermentation and Simultaneous Saccharification and Co-Fermentation." BioResources 6.4 (2011): 3791-3808.
Prasetyo, Joni, and Enoch Y. Park. "Waste paper sludge as a potential biomass for bio-ethanol production." Korean Journal of Chemical Engineering 30.2 (2013): 253-261.
Shammas, Nazih K., Lawrence K. Wang, and Mark Landin. "Treatment of Paper Mill Whitewater, Recycling and Recovery of Raw Materials." Flotation Technology (2010): 221-268.
Wang, Lei, Richard Templer, and Richard J. Murphy. "A Life Cycle Assessment (LCA) comparison of three management options for waste papers: bioethanol production, recycling and incineration with energy recovery." Bioresource Technology (2012).
Kang, Li, Wei Wang, and Yoon Y. Lee. "Bioconversion of kraft paper mill sludges to ethanol by SSF and SSCF." Applied biochemistry and biotechnology 161.1 (2010): 53-66.
Pan, Xuejun, et al. "Biorefining of softwoods using ethanol organosolv pulping: Preliminary evaluation of process streams for manufacture of fuel-grade ethanol and co-products." Biotechnology and Bioengineering 90.4 (2005): 473-481.
Lark, Nicole, et al. "Production of ethanol from recycled paper sludge using cellulase and yeast, Kluveromyces marxianus" Biomass and Bioenergy 12.2 (1997): 135-143.
Fan, Zhiliang, et al. "Conversion of paper sludge to ethanol in a semicontinuous solids-fed reactor." Bioprocess and biosystems engineering 26.2 (2003): 93-101.
Jeffries, Thomas W., and Richard Schartman. "Bioconversion of secondary fiber fines to ethanol using counter-current enzymatic saccharification and co-fermentation." Applied biochemistry and biotechnology 78.1 (1999): 435-444.
Jin, Yongcan, et al. "Green liquor pretreatment of mixed hardwood for ethanol production in a repurposed kraft pulp mill." Journal of Wood Chemistry and Technology 30.1 (2010): 86-104.
Fan, Zhiliang, and Lee R. Lynd. "Conversion of paper sludge to ethanol, II: process design and economic analysis." Bioprocess and biosystems engineering 30.1 (2007): 35-45.

(56) References Cited

OTHER PUBLICATIONS

Da Silva, Roberto, Dong K. Yim, and Yong K. Park. "Application of thermostable xylanases from *Humicola* sp. for pulp improvement." Journal of fermentation and bioengineering 77.1 (1994): 109-111.

Hu, Gang, John A. Heitmann, and Orlando J. Rojas. "Feedstock pretreatment strategies for producing ethanol from wood, bark, and forest residues." BioResources 3.1 (2008): 270-294.

Saha, Badal C. "Hemicellulose bioconversion." Journal of industrial microbiology & biotechnology 30.5 (2003): 279-291.

Gáspár, Melinda, Gergely Kálmán, and Kati Réczey. "Corn fiber as a raw material for hemicellulose and ethanol production." Process Biochemistry 42.7 (2007): 1135-1139.

Zhang, Jiayi, and Lee R. Lynd. "Ethanol production from paper sludge by simultaneous saccharification and co-fermentation using recombinant xylose-fermenting microorganisms." Biotechnology and bioengineering 107.2 (2010): 235-244.

\* cited by examiner

Enzymatic hydrolysis yield of different substrates. Enzyme was added 50 FPU of *T. reesei* and the hydrolysis was conducted at 50 °C for 3 days.

Enzymatic hydrolysis yield of a bleached hardwood kraft pulp (Eucalyptus, Baycel). Different enzyme formulations.

Filler effect on UKP hydrolysis yield. UKP (■), UKP with 30% of Kaolin (▲), UKP with 30% of CaCO$_3$ (♦) and replication n=2, α=0.05.

Hydrolysis yield of UKP and CaCO$_3$ (15%) mixture depending on different Tween-80 dosage with 20 FPU of *T. reesei*

Hydrolysis yield of fines depending on different Tween-80 dosage with 20 FPU of *T. reesei*

Hydrolysis yield of fines combined diverse dosage of Tween-80

Tween-80 (3%) effect on hydrolysis yield of UKP and mixture material of UKP and fillers. UKP (♦), UKP with Tween-80 (■), UKP + CaCO$_3$ (15%) + Kaolin (15%) (-), UKP + CaCO$_3$ (15%) + Kaolin (15%) with Tween-80 (●) and replication n=2, α=0.05.

Combination effect of Tween-80 (3%) and low pH buffer for hydrolysis yield. Fines only (■), Fines with 3% of Tween-80 (▲), Fines with Tween-80 and pH4 buffer (♦) and replication n=2, α=0.05.

Temperature effect on hydrolysis of pure fines and surfactant mixed fines. Fines with Tween-80 (3%) at 50°C (▲), Fines at 50°C (■), Fines at 55°C (◆), Fines with Tween-80 (3%) at 55°C (●) and replication n=2, α=0.05.

ENZYMATIC HYDROLYSIS OF OLD CORRUGATED CARDBOARD (OCC) FINES FROM RECYCLED LINERBOARD MILL WASTE REJECTS

CROSS REFERENCE TO RELATED APPLICATION

The present application is a non-provisional of, and claims priority from, U.S. Provisional Patent Application No. 61/953,152, filed Mar. 14, 2014, the entirety of which is expressly incorporated herein by reference.

FIELD OF THE INVENTION

This invention relates to processing of cellulosic solid waste from paper related industries for extraction of fermentable sugars.

BACKGROUND OF THE INVENTION

Rising oil prices, unstable supply and the demand for sustainable environmental friendly energy sources has increase the interest in research and development of bio-energy sources such as bio-ethanol. Carbohydrates are a natural resource commonly available as lignocellulosic biomass that can be hydrolyzed into sugars to be further converted via fermentative or thermochemical processes into useful products [1]. Among the important products that can be derived are ethanol (cellulosic), butanol and similar advanced fuels, platform chemicals such as acetone, furfural, levulinic acid, gamma valerolactone and bioplastics such as polyhydroxy butyrates or valerates [1-3]. These products are a substitute for fossil fuels or starch based carbohydrates, thus providing an alternate sustainable resource. The plastics are biodegradable and thus are beneficial to the environment in comparison to petrochemicals and their derivatives [4]. Cellulosic biomass is a promising material for bio-energy that avoids the usage of corn and other food grains and thus avoids the necessity of competing with edible sugars.

One of the biggest markets using cellulosic biomass is the pulp and paper industry. The global production of paper and paperboard was 403 million tons in 2011. This amount is about 30% of the industrial round-wood. The recycling rate of paper has been gradually increasing from 50% in 2007 to 53% in 2011. North America now has the highest recovery rate (64% in 2011), followed by Europe (58%) and the Asia-Pacific region (48%) [5]. This process of recycling pulp and papers is to reduce cost and to have a sustainable environmental policy. [6-8].

Repeated recycling of pulp decreases the length of fibers which become shorter and stiffer, losing their ability to bond within the paper sheet. At a certain stage, their net contribution to the sheet becomes negative and they need to be rejected. These short fibers known as fines are recovered from the wastewater stream and typically sent to landfills. The solid residue can also be applied for land use or animal bedding [9-12]. However, the fines can be a very useful resource for sugar production because they are predominantly composed of cellulose which could be converted into glucose and other monomeric sugars. Currently, some paper companies pay $25 to $80/(wet) ton for disposal of the fines [9, 13, 14]. Besides their cost advantage, the supply of fines from paper mills is fairly homogeneous and thus there is minimal influence of seasonal or weather related supply challenges compared to other agricultural biomass [6, 8].

A number of different processes including incineration, gasification and pyrolysis may be used for treating this waste fines stream [10]. However, given their energy consumption and complex processes, direct hydrolysis of the cellulose into sugars can be particularly attractive due to the simplicity of the process and ready use of the sugar solution after concentration [15]. These sugars can be used as a feedstock for conversions into biofuels and bioplastics such as polyhydroxy alkanoates or into platform chemicals such as succinic acid, lactic acid, levulinic acid and furfurals [1, 16-18].

Of the varieties of papermill fines rejects, those from recycled pulp mills using old corrugated cartons are particularly important. Some modern OCC mills find that rejecting 'inactive' fines into the waste stream can be more profitable than using them in the manufactured product, particularly recycled linerboard. The reject stream thus contains higher cellulosic fines contents and typically lower minerals than deinked pulp rejects in the waste streams of fine papers or tissue mills.

Lignocellulosic materials are excellent sources for energy products, platform chemicals and bioplastics. Sugars produced by the degradation of carbohydrate polymers can be fermented into ethanol and butanol as energy sources. Sugars and cellulose degradation compounds can serve as platform chemicals in the production of bulk chemicals and they can also be used as feedstocks for microbial production of plastics such as polyhydroxy alkanoates (PHA).

The waste stream from recycled paper mills contains cellulosic fines and also particles of mineral origin, typically clay or calcium carbonate from the fillers and coatings used in the waste paper. The cellulosic fines are easily hydrolyzable by either acid or enzymatic processes. In the enzymatic process, a cocktail of cellulose enzymes acts progressively and sequentially to open up the cellulose crystalline structure and depolymerize it, producing monomeric sugars. The sugars are primarily glucose and certain other common hexoses which are fermentable into ethanol, butanol or other products, leading to bioplastics such as polyhydroxy alkanoates (PHA).

See, U.S. Pat. Nos. and Published patent application Nos. 8,395,023; 8,394,617; 8,394,616; 8,389,260; 8,389,259; 8,389,258; 8,389,257; 8,389,256; 8,389,255; 8,389,254; 8,377,659; 8,372,598; 8,367,819; 8,362,322; 8,361,767; 8,361,762; 8,357,523; 8,354,263; 8,343,747; 8,334,430; 8,328,947; 8,323,947; 8,318,461; 8,317,975; 8,309,328; 8,298,802; 8,298,799; 8,298,795; 8,293,508; 8,288,148; 8,288,144; 8,283,150; 8,278,260; 8,278,079; 8,273,559; 8,257,959; 8,247,647; 8,247,203; 8,241,881; 8,241,461; 8,236,551; 8,236,546; 8,236,542; 8,236,535; 8,232,080; 8,227,236; 8,217,227; 8,216,815; 8,212,087; 8,206,964; 8,206,963; 8,202,831; 8,202,709; 8,192,968; 8,178,336; 8,173,410; 8,168,038; 8,158,397; 8,148,579; 8,148,133; 8,143,480; 8,143,050; 8,142,620; 8,133,711; 8,119,385; 8,114,974; 8,114,655; 8,101,398; 8,101,393; 8,101,024; 8,097,445; 8,097,442; 8,093,037; 8,092,647; 8,083,906; 8,080,398; 8,071,351; 8,071,349; 8,067,222; 8,063,201; 8,061,362; 8,043,839; 8,043,837; 8,034,592; 8,030,050; 8,017,820; 8,017,372; 8,008,056; 7,998,711; 7,993,898; 7,993,890; 7,993,463; 7,981,646; 7,981,644; 7,981,643; 7,977,450; 7,972,832; 7,967,904; 7,964,383; 7,960,528; 7,960,160; 7,960,151; 7,960,148; 7,960,146; 7,954,734; 7,951,571; 7,951,570; 7,947,813; 7,946,295; 7,943,363; 7,939,488; 7,932,072; 7,932,065; 7,931,784; 7,927,854; 7,923,236; 7,923,235; 7,923,233; 7,910,347; 7,906,704; 7,901,511; 7,887,862; 7,875,292; 7,867,745; 7,838,666; 7,829,732; 7,816,581; 7,811,799; 7,810,507; 7,807,434;

7,803,601; 7,786,351; 7,786,350; 7,785,854; 7,754,457; 7,741,089; 7,732,173; 7,727,754; 7,727,746; 7,723,568; 7,709,697; 7,682,811; 7,670,813; 7,659,099; 7,651,582; 7,642,079; 7,632,479; 7,611,882; 7,601,529; 7,592,434; 7,592,163; 7,585,652; 7,582,462; 7,547,534; 7,527,959; 7,504,120; 7,503,981; 7,459,299; 7,452,707; 7,449,550; 7,449,319; 7,431,942; 7,407,788; 7,399,855; 7,399,485; 7,381,553; 7,361,736; 7,351,573; 7,351,568; 7,344,871; 7,320,886; 7,273,742; 7,226,773; 7,226,772; 7,198,925; 7,183,093; 7,172,891; 7,144,716; 7,083,673; 7,070,805; 7,067,303; 7,056,721; 7,049,125; 7,048,952; 7,045,332; 7,045,331; 7,033,811; 7,005,289; 6,982,159; 6,911,565; 6,908,995; 6,894,199; 6,878,199; 6,855,531; 6,818,434; 6,815,192; 6,768,001; 6,713,460; 6,630,340; 6,620,605; 6,566,114; 6,555,335; 6,555,228; 6,500,658; 6,451,063; 6,444,653; 6,420,165; 6,399,351; 6,387,690; 6,333,181; 6,328,994; 6,268,197; 6,268,196; 6,228,630; 6,207,436; 6,197,564; 6,174,700; 6,153,413; 6,140,105; 6,132,998; 6,130,076; 6,110,712; 6,080,567; 6,074,856; 6,069,136; 6,048,715; 6,017,740; 6,013,490; 6,010,870; 6,008,176; 6,005,141; 6,001,639; 5,989,887; 5,962,278; 5,962,277; 5,908,649; 5,885,819; 5,874,276; 5,871,550; 5,866,392; 5,863,783; 5,861,271; 5,792,630; 5,786,313; 5,770,010; 5,747,082; 5,705,369; 5,693,518; 5,683,911; 5,554,520; 5,518,902; 5,505,950; 5,503,996; 5,487,989; 5,464,832; 5,458,899; 5,437,992; 5,424,417; 5,424,202; 5,416,210; 5,395,623; 5,395,455; 5,391,561; 5,302,592; 5,300,672; 5,292,762; 5,179,127; 5,171,570; 5,170,620; 5,166,390; 5,151,447; 5,149,524; 5,118,681; 5,112,382; 5,102,898; 5,091,399; 5,081,026; 5,059,654; 5,055,308; 5,037,663; 5,023,275; 4,975,459; 4,950,597; 4,851,394; 4,831,127; 4,713,118; 4,694,906; 4,628,029; 4,594,130; 4,540,587; 4,431,675; 4,321,360; 4,321,328; 4,321,278; 4,292,406; 4,275,163; 4,260,685; 4,235,968; 4,058,411; 4,017,642; 3,990,944; 20130065270; 20130060070; 20130052713; 20130052698; 20130052694; 20130052693; 20130046120; 20130046119; 20130046032; 20130045891; 20130040352; 20130035525; 20130035524; 20130035523; 20130035522; 20130035521; 20130035520; 20130035519; 20130035518; 20130035516; 20130034891; 20130034888; 20130032466; 20130030215; 20130029382; 20130023608; 20130014293; 20130012424; 20130011895; 20130011887; 20130011886; 20120329104; 20120329100; 20120329096; 20120323525; 20120323050; 20120323049; 20120322121; 20120322078; 20120321581; 20120316376; 20120316330; 20120315683; 20120309060; 20120301944; 20120291160; 20120289607; 20120289450; 20120283493; 20120282664; 20120277491; 20120277490; 20120277489; 20120277488; 20120277487; 20120277486; 20120277485; 20120277483; 20120277482; 20120277481; 20120277480; 20120276595; 20120276594; 20120273339; 20120273338; 20120270298; 20120270289; 20120270278; 20120270270; 20120266329; 20120266328; 20120264107; 20120252085; 20120245336; 20120238785; 20120237984; 20120237983; 20120231510; 20120220513; 20120216705; 20120214209; 20120211184; 20120210467; 20120209034; 20120208235; 20120199299; 20120199298; 20120196338; 20120190840; 20120190076; 20120190054; 20120184020; 20120184007; 20120178975; 20120165562; 20120165517; 20120164709; 20120164696; 20120159840; 20120159839; 20120157725; 20120157721; 20120156754; 20120156741; 20120156162; 20120156161; 20120156160; 20120156159; 20120156158; 20120156157; 20120156156; 20120156155; 20120151827; 20120149949; 20120149077; 20120149065; 20120146468; 20120142886; 20120142068; 20120142065; 20120142046; 20120135500; 20120135499; 20120135489; 20120129696; 20120129229; 20120111321; 20120108798; 20120107892; 20120107888; 20120107887; 20120107881; 20120107880; 20120101250; 20120100587; 20120100045; 20120094358; 20120094355; 20120094343; 20120083019; 20120079665; 20120077247; 20120077216; 20120066781; 20120064609; 20120064592; 20120064579; 20120059197; 20120052534; 20120046501; 20120045812; 20120045811; 20120041075; 20120040435; 20120040409; 20120036769; 20120036768; 20120036599; 20120035400; 20120030838; 20120029247; 20120028325; 20120028306; 20120021490; 20120021092; 20120015422; 20120015408; 20120010448; 20120010447; 20120010446; 20120010445; 20120010444; 20120010443; 20120010440; 20120010439; 20120010438; 20120010437; 20120010436; 20120009640; 20120009634; 20120009631; 20120006320; 20120005949; 20120003704; 20120003703; 20120003701; 20110319849; 20110318798; 20110318796; 20110315154; 20110314726; 20110312058; 20110312055; 20110312048; 20110306117; 20110306083; 20110300586; 20110296555; 20110296543; 20110294181; 20110294165; 20110294164; 20110275130; 20110271875; 20110269201; 20110268858; 20110262985; 20110262984; 20110251377; 20110250674; 20110250667; 20110250638; 20110250635; 20110239333; 20110237769; 20110236339; 20110236338; 20110236337; 20110236336; 20110236335; 20110233042; 20110232164; 20110232163; 20110232162; 20110232161; 20110232160; 20110229959; 20110229956; 20110224416; 20110212505; 20110212499; 20110207192; 20110190488; 20110185456; 20110183379; 20110178261; 20110177573; 20110177565; 20110177561; 20110171709; 20110171705; 20110165661; 20110165660; 20110159544; 20110155559; 20110152812; 20110152370; 20110152369; 20110152368; 20110150857; 20110146138; 20110144241; 20110143398; 20110139662; 20110139659; 20110139658; 20110139657; 20110138502; 20110136908; 20110136907; 20110136196; 20110136174; 20110130488; 20110129887; 20110129881; 20110129880; 20110125118; 20110124074; 20110124058; 20110117619; 20110117067; 20110111456; 20110100359; 20110097786; 20110095111; 20110093965; 20110091950; 20110091940; 20110086410; 20110086408; 20110081697; 20110081412; 20110081336; 20110081335; 20110076743; 20110065910; 20110061666; 20110053245; 20110046422; 20110045544; 20110040058; 20110039320; 20110039317; 20110039309; 20110039308; 20110035839; 20110035838; 20110033391; 20110028672; 20110027837; 20110027346; 20110020874; 20110016545; 20110014672; 20110003345; 20110003341; 20110000125; 20100330633; 20100319862; 20100317087; 20100317059; 20100312028; 20100304440; 20100304439; 20100298612; 20100297721; 20100297704; 20100287826; 20100285534; 20100279361; 20100279354; 20100273214; 20100268000; 20100267110; 20100263264; 20100240128; 20100223694; 20100221819; 20100221784; 20100216200; 20100212091; 20100196978; 20100196977; 20100189706; 20100184178; 20100184175; 20100179315; 20100167371; 20100167370; 20100160201; 20100159566; 20100159553; 20100159510; 20100151551; 20100151547; 20100151546; 20100144584; 20100143998; 20100137647; 20100136661; 20100136113; 20100129835; 20100124583; 20100113846; 20100112242; 20100108567; 20100107342; 20100105114; 20100101605; 20100099640; 20100095390; 20100087687; 20100086978; 20100068790; 20100068768; 20100056774; 20100055753; 20100055747; 20100048964; 20100048417; 20100041104; 20100035320; 20100031398; 20100028966; 20100021988; 20100011456; 20100003733; 20100003716; 20100003234; 20090325254; 20090324574; 20090312537; 20090312221; 20090311752; 20090298149; 20090297495; 20090286295; 20090286294; 20090280105; 20090258172; 20090247448; 20090235388; 20090234142; 20090233335; 20090226979; 20090224086; 20090221051; 20090220480; 20090217569;

20090209009; 20090203102; 20090202675; 20090198046; 20090194243; 20090181433; 20090181126; 20090176292; 20090172838; 20090170747; 20090170181; 20090163397; 20090155238; 20090142848; 20090136476; 20090099079; 20090098266; 20090093028; 20090081762; 20090075336; 20090070898; 20090068714; 20090061490; 20090042266; 20090042259; 20090038023; 20090036648; 20090035826; 20090025739; 20090025738; 20090017512; 20090013434; 20090005532; 20090004726; 20080311640; 20080305531; 20080293114; 20080293086; 20080292747; 20080292701; 20080274527; 20080261267; 20080254080; 20080248160; 20080241900; 20080233175; 20080229657; 20080229456; 20080227173; 20080206836; 20080202684; 20080201801; 20080193981; 20080176282; 20080145912; 20080138880; 20080113413; 20080102502; 20080095889; 20080085536; 20080085520; 20080076314; 20080076152; 20080070291; 20080064906; 20080056983; 20080034453; 20080029110; 20080020435; 20080009047; 20070298475; 20070254031; 20070219521; 20070213249; 20070207530; 20070202566; 20070199095; 20070192903; 20070178569; 20070173431; 20070172916; 20070149777; 20070148751; 20070148730; 20070141693; 20070141660; 20070118918; 20070118917; 20070113302; 20070113301; 20070105112; 20070094748; 20070092935; 20070092934; 20070089196; 20070089195; 20070089194; 20070089193; 20070089192; 20070089191; 20070089190; 20070089189; 20070089188; 20070089187; 20070089186; 20070089185; 20070089184; 20070087066; 20070083952; 20070083951; 20070083950; 20070083949; 20070083947; 20070079944; 20070072185; 20070059813; 20070036832; 20070031954; 20070011775; 20060281157; 20060275241; 20060259995; 20060258554; 20060255507; 20060235115; 20060211101; 20060210971; 20060205042; 20060200878; 20060188965; 20060182802; 20060166322; 20060165613; 20060154844; 20060154352; 20060141601; 20060135388; 20060110797; 20060104931; 20060089283; 20060084156; 20060068475; 20060057672; 20060046284; 20060035353; 20060018862; 20060003433; 20050277172; 20050272836; 20050244934; 20050244878; 20050221369; 20050214921; 20050210548; 20050125860; 20050120915; 20050100996; 20050070003; 20050054039; 20050037459; 20050009166; 20040266642; 20040259218; 20040231661; 20040210099; 20040203134; 20040157301; 20040121436; 20040102619; 20040067569; 20040053238; 20030225005; 20030216492; 20030203466; 20030203454; 20030180900; 20030125588; 20030119006; 20030114330; 20030113735; 20030113734; 20030113732; 20030097029; 20030092097; 20030087415; 20030082779; 20030054539; 20030054518; 20030054500; 20030032162; 20030032148; 20030032084; 20030022807; 20020193272; 20020164774; 20020160469; 20020156048; 20020142034; 20020045057; 20020012980; 20010044138; 20010010825, each of which is expressly incorporated herein by reference.

See also,

Van Heiningen, Adriaan. "Converting a kraft pulp mill into an integrated forest products biorefinery." *ANNUAL MEETING-PULP AND PAPER TECHNICAL ASSOCIATION OF CANADA*. Vol. 92. No. C. Pulp and Paper Technical Association of Canada; 1999, 2006.

Zhu, J. Y., and X. J. Pan. "Woody biomass pretreatment for cellulosic ethanol production: technology and energy consumption evaluation." *Bioresource technology* 101.13 (2010): 4992-5002.

Pérez, J., et al. "Biodegradation and biological treatments of cellulose, hemicellulose and lignin: an overview." *International Microbiology* 5.2 (2002): 53-63.

Kadam, Kiran L., Chim Y. Chin, and Lawrence W. Brown. "Flexible biorefinery for producing fermentation sugars, lignin and pulp from corn stover." *Journal of industrial microbiology & biotechnology* 35.5 (2008): 331-341.

Kuhad, Ramesh Chander, and Ajay Singh. "Lignocellulose biotechnology: current and future prospects." *Critical Reviews in Biotechnology* 13.2 (1993): 151-172.

Lawford, Hugh G., and Joyce D. Rousseau. "Production of ethanol from pulp mill hardwood and softwood spent sulfite liquors by genetically engineered *E. coli.*" *Applied biochemistry and biotechnology* 39.1 (1993): 667-685.

Burchhardt, G., and L. O. Ingram. "Conversion of xylan to ethanol by ethanologenic strains of *Escherichia coli* and *Klebsiella oxytoca.*" *Applied and environmental microbiology* 58.4 (1992): 1128-1133.

Zhu, J. Y., Ronald Sabo, and Xiaolin Luo. "Integrated production of nano-fibrillated cellulose and cellulosic biofuel (ethanol) by enzymatic fractionation of wood fibers." *Green Chemistry* 13.5 (2011): 1339-1344.

Hoge, William H. "Process for making ethanol and fuel product." U.S. Pat. No. 4,321,328. 23 Mar. 1982.

López-Contreras, Ana M., et al. "Utilisation of saccharides in extruded domestic organic waste by *Clostridium acetobutylicum* ATCC 824 for production of acetone, butanol and ethanol." *Applied microbiology and biotechnology* 54.2 (2000): 162-167.

Zhang, Xiao, et al. "High consistency enzymatic hydrolysis of hardwood substrates." *Bioresource technology* 100.23 (2009): 5890-5897.

Kirk, T. Kent, T. W. Jeffries, and George F. Leatham. "Biotechnology: applications and implications for the pulp and paper industry." *Tappi J* 66.5 (1983): 45-51.

Yamashita, Yuya, et al. "Ethanol production from paper sludge by immobilized *Zymomonas mobilis.*" *Biochemical Engineering Journal* 42.3 (2008): 314-319.

Lee, Sang-Mok, Jianqiang Lin, and Yoon-Mo Koo. "Hydrolysis of Paper Sludge Using Mixed Cellulase System: Enzymtic Hydrolysis of Paper Sludge." *ACS Symposium Series*. Vol. 830. Washington, D.C.; American Chemical Society; 1999, 2002.

Kang, Li, et al. "Enhanced Ethanol Production from De-Ashed Paper Sludge by Simultaneous Saccharification and Fermentation and Simultaneous Saccharification and Co-Fermentation." *BioResources* 6.4 (2011): 3791-3808.

Chen, Hui, et al. "Enzymatic Hydrolysis of Recovered Office Printing Paper with Low Enzyme Dosages to Produce Fermentable Sugars." *Applied biochemistry and biotechnology* (2012): 1-16.

McManigal, Brent Alan. "System And Method For Producing Ethanol From Paper Mill Sludge." U.S. patent application Ser. No. 11/735,633.

Elliston, Adam, et al. "High concentrations of cellulosic ethanol achieved by fed batch semi simultaneous saccharification and fermentation of waste-paper." *Bioresource Technology* (2013).

Shammas, Nazih K., Lawrence K. Wang, and Mark Landin. "Treatment of Paper Mill Whitewater, Recycling and Recovery of Raw Materials." *Flotation Technology* (2010): 221-268.

Kang, Li. *Bioconversion of Pulp and Paper Mills Sludge and Prehydrolysate Stream into Ethanol and Cellulase Enzyme*. Diss. Auburn University, 2011.

Prasetyo, Joni, and Enoch Y. Park. "Waste paper sludge as a potential biomass for bio-ethanol production." *Korean Journal of Chemical Engineering* 30.2 (2013): 253-261.

Ichiura, Hideaki, Takuhiro Nakatani, and Yoshito Ohtani. "Separation of pulp and inorganic materials from paper sludge using ionic liquid and centrifugation." *Chemical Engineering Journal* 173.1 (2011): 129-134.

Wang, Lei, Richard Templer, and Richard J. Murphy. "A Life Cycle Assessment (LCA) comparison of three management options for waste papers: bioethanol production, recycling and incineration with energy recovery." *Bioresource Technology* (2012).

Kang, Li, Wei Wang, and Yoon Y. Lee. "Bioconversion of kraft paper mill sludges to ethanol by SSF and SSCF." *Applied biochemistry and biotechnology* 161.1 (2010): 53-66.

Pan, Xuejun, et al. "Biorefining of softwoods using ethanol organosolv pulping: Preliminary evaluation of process streams for manufacture of fuel-grade ethanol and co-products." *Biotechnology and Bioengineering* 90.4 (2005): 473-481.

Lark, Nicole, et al. "Production of ethanol from recycled paper sludge using cellulase and yeast, *Kluveromyces marxianus*" *Biomass and Bioenergy* 12.2 (1997): 135-143.

Fan, Zhiliang, et al. "Conversion of paper sludge to ethanol in a semicontinuous solids-fed reactor." *Bioprocess and biosystems engineering* 26.2 (2003): 93-101.

Jeffries, Thomas W., and Richard Schartman. "Bioconversion of secondary fiber fines to ethanol using countercurrent enzymatic saccharification and co-fermentation." *Applied biochemistry and biotechnology* 78.1 (1999): 435-444.

Jin, Yongcan, et al. "Green liquor pretreatment of mixed hardwood for ethanol production in a repurposed kraft pulp mill." *Journal of Wood Chemistry and Technology* 30.1 (2010): 86-104.

Fan, Zhiliang, and Lee R. Lynd. "Conversion of paper sludge to ethanol, II: process design and economic analysis." *Bioprocess and biosystems engineering* 30.1 (2007): 35-45.

Da Silva, Roberto, Dong K. Yim, and Yong K. Park. "Application of thermostable xylanases from *Humicola* sp. for pulp improvement." *Journal of fermentation and bioengineering* 77.1 (1994): 109-111.

Hu, Gang, John A. Heitmann, and Orlando J. Rojas. "Feedstock pretreatment strategies for producing ethanol from wood, bark, and forest residues." *BioResources* 3.1 (2008): 270-294.

Villavicencio, Eduardo J., and Jose B. Dos Santos. "Process to produce a high quality paper product and an ethanol product from bamboo." U.S. Pat. No. 5,198,074. 30 Mar. 1993.

Gáspár, Melinda, Gergely Kálmán, and Kati Réczey. "Corn fiber as a raw material for hemicellulose and ethanol production." *Process Biochemistry* 42.7 (2007): 1135-1139.

Zhang, Jiayi, and Lee R. Lynd. "Ethanol production from paper sludge by simultaneous saccharification and co-fermentation using recombinant xylose-fermenting microorganisms." *Biotechnology and bioengineering* 107.2 (2010): 235-244.

Saha, Badal C. "Hemicellulose bioconversion." *Journal of industrial microbiology & biotechnology* 30.5 (2003): 279-291.

Each of the foregoing references is expressly incorporated herein by reference in its entirety.

SUMMARY OF THE INVENTION

The present technology study focuses on the enzymatic hydrolysis of OCC fines rejects from a recycled linerboard mill. The saccharification of this waste stream to yield fermentable sugars was identified and optimized using different commercially available enzyme mixtures. The effect of enzyme activity (characterized by their FPUs), impact of hydrolysis temperature, pH, pulp type, filler composition were investigated. Furthermore, methods of enhancing the enzyme activity and sugar yields by binding the minerals using different surfactants (cationic and nonionic) were also investigated.

A significant fraction of short fibers commonly called as fines is produced while recycling OCC (Old Corrugated Containerboards). These fines are usually rejected as solid waste stream that further requires landfilling and poses environmental problems. The major component of these fines rejects are primarily cellulose that can be hydrolyzed into sugars for possible fermentation into biofuels, bioplastics or other sugar based products.

In addition to environmental advantages, use of these fines also offers benefits such as negative costs and production of fermentable sugars without requiring any complex pretreatment processes that are required to hydrolyze and eliminate inhibitors from hydrolyzate.

According to the present technology, enzymatic hydrolysis of reject fines from a recycled OCC mill was performed. Different strains of cellulases were tested for their compatibility and *Trichoderma Reesei* was found to be the most effective at loading levels of 5-50 FPU (/g of oven dry mass). A maximum hydrolysis yield of 43% sugar (g/g-OD fines) with 50 FPU was observed. See, Byeong Cheol Min, Bhavin V. Bhayani, Bandaru V. Ramarao, "Enzymatic Hydrolysis of Old Corrugated Cardboard (OCC) Fines from Recycled Linerboard Mill Waste Rejects", Proc. AICHE 2013 (Nov. 3-8), extended abstract P346631, expressly incorporated herein by reference.

The presence of fillers (up to 30% by mass) in the fines increases the required dosage of enzymes that increases the costs of hydrolysis.

It was found that the required enzyme loading can be lowered by addition of nonionic surfactants to reduce their inhibitory activity. The nonionic surfactant Triton X-80 improved hydrolysis yields by up to 10 percent points.

Paper mill rejected fines are a good source of biomass for sugar production given the low lignin content (Table 1), negative price, pre-processed nature which negates requirement of a pretreatment regime and the larger surface area and porous nature of the particles compared to other naturally occurring biomass. The particle size of about 3 µm is much smaller than typically milled biomass particles whose sizes are in the sub-millimeter ranges. The enzymatic hydrolysis yield of fines achieved was up to 70% of reducing sugars from fermentable sugars in the fines. The sugar yield of rejected fines is similar to the hydrolysis yield of woody biomass which was reported as 70% to 90% for lignocellulosic biomass [3, 19].

TABLE 1

Characteristics of fines of rejected sludge from OCC paper mill

| Fines (rejected fines containing fillers and contaminants) | Value |
|---|---|
| pH | 6.4 |
| Solid content | 0.52% |
| Particle size | 2.1-3 µm |
| Zeta Potential | (−) 9 m V |
| Lignin | 3% |
| Ash content Analysis | |
| Total | 33% |
| Calcium Carbonate | 15% |
| Other fillers and residuals | 18% |

The commercialization of "waste cellulosic fiber" based sugar requires deactivation of inhibitory potential of contaminants and ash which includes fillers, calcium carbonate being one of the most powerful inhibitors [20]. Several surfactants were studied to improve enzymatic hydrolysis. Even though the precise mechanism and principle were not defined, many surfactant studies have concluded the feasibility of surfactant for advanced enzymatic hydrolysis [21-27]. Addition of non-ionic surfactant Tween-80 improved hydrolysis yield of mixture of UKP and $CaCO_3$ in various enzyme dosage (FIG. 6). The required enzyme dosage for complete hydrolysis (about 70% sugar conversion) was reduced from 50 FPU to 30 FPU for the fines (FIG. 7). Using the surfactant it was possible to minimize enzyme dosage for maximum hydrolysis yield which is important for economic sugar production.

The optimum dosage of surfactant was in range of up to 10%. Excessive dosage (above 10%) caused agglutination of substrates and thus a decreased hydrolysis yield. Other studies suggested similar dosage of surfactant for enzymatic hydrolysis [21, 24, 27]. Our research indicated a dosage of 7% for the synthetic fines mixed UKP and $CaCO_3$ (15%) but presented wide range of surfactant dosage (3 to 9%) for the fines. Application of pH 4 buffer instead of pH 5 buffer increased hydrolysis yield and decreased enzyme dosage for maximum hydrolysis yield (FIG. 8). The yield improvement of the combination method was more significant at the 10 FPU enzyme dosage. The demand of low pH buffer is regarded due to $CaCO_3$ in the fines. Adjusting pH is good for not only optimizing hydrolysis condition for enzyme but also dissolving calcium carbonate from fibers.

The presence of fillers and crystalline fibers are considered as primary inhibitors for the hydrolysis process while presence of other contaminants such as inks have a lesser inhibitory potential and thus can be classified as secondary inhibitors based upon their inhibitory activity. The process of drying fines is to be avoided for effective enzymatic hydrolysis. The enzymatic hydrolysis yield of both the fines and UKP was decreased by about 30% after drying (Table 2) which is due to decreased accessibility of micro-fibrils. To increase accessibility of cellulose, dissolving in alkaline method can be applied [28]. Beating method is also studied for recycled fiber to increase accessibility of cellulose by increasing swelling ability, water retention value, pore size and pore volume [29].

TABLE 2

Drying effect of materials on enzymatic hydrolysis yield (replication n = 2).

| 25 FPU, 3 days | Hydrolysis yield (%, g/g) | | |
| --- | --- | --- | --- |
| | Non-dried | Dried | Dry Effect (%) |
| Fines | 30.35 (±1.38) | 21.41 (±2.1) | −29.5 |
| Unbleached Kraft Pulp | 92.11 (±0.8) | 64.06 (±0.4) | −30.5 |

Even though enzyme dosage was reduced from 50 FPU to around 25 FPU for 1 g of fine maximum hydrolysis yield by combination process, 25 FPU is still high demand of enzyme and not profitable. The development of contaminants separation and surfactant injection is expected to make profitable enzyme dosage and high yield of sugar from fines.

The fines have a potential to produce sugars as a resource of biomass. The main inhibitor of enzymatic hydrolysis fines was $CaCO_3$ (15% of fines) which is decreasing enzyme activity by adsorption and increase of pH. Nonionic surfactant, 3-9% of Tween-80, improved enzymatic hydrolysis yield of paper industrial waste fines in addition of 50% increase at 10 FPU and reduced enzyme dosage of *Trichoderma reesei* ATCC 26921 for the maximum yield. The surfactant application was simple and an economical option to increase profitability and productivity of sugars from waste cellulosic fibers by improving enzyme activity. Using proper pH buffer for optima enzymatic hydrolysis condition pH 5 was also a considerable method for economical sugar production from fines. It was found that addition of surfactants and acid mitigated inhibitor effect of $CaCO_3$ which has a high inhibitory potential. Also, separation processes to reduce fillers and contaminants from fines is considered to save more enzymes.

The present technology processes a waste stream comprising cellulosic fines, e.g., from recycled packaging paper mills, into a stream of fermentable sugars. These may be fermented to yield bioethanol which is of value as a fuel, and/or manufacturers of other products such as bioplastics such as polyhydroxy alkanoates.

According to a preferred embodiment, a process is provided to:

(a) hydrolyze the cellulosic fines found in recycled paper mill waste streams using a commercially available cellulose enzyme formulation;

(b) increase the enzymatic hydrolysis yield by shielding the inert components of the waste stream using a surfactant; and (c) optimize the surfactant with respect to its composition (anionic, non-ionic or cationic) and dosage.

The enzymes, however, may have a competitive binding affinity for inorganic particulates, resulting in a non-specific absorption of some or all types of enzymes to the particles. Indeed, similar high surface area particles are used in the purification of similar enzymes. Therefore, in the presence of inorganic particles, such as precipitated calcium chloride (PCC), the activity and bioavailability of the enzymes may be substantially reduced.

It has been found that surfactants are able to coat the inorganic particulates and otherwise reduce binding of the hydrolytic enzymes, leading to a significant increase in activity, thus saving cost and increasing efficiency. It has been found that effective surfactants do not also block binding or biological activity of the enzymes for the cellulosic particles and components of the solution.

Cationic, non-ionic and anionic surfactants were tested at various dosages. A non-ionic surfactant, Tween 80 (polysorbate 80) was better than the cationic and anionic surfactants.

The inorganic particles may be separated from the waste stream.

Some investigators have suggested the use of anaerobic fermentation as a means to degrade the organic components in the waste stream, but due to presence of large amount of calcium carbonate, kaolin and other fillers, they give rise to problems such as scaling of biomass, reactors and pipes, reduced specific methanogenic activity and loss of buffer capacity, and essential nutrients for anaerobic degradation.

Commercially available hydrolysis enzymes include Cellic® HTec3, a concentrated hemicellulase that works alone or in combination with Cellic® CTec3 cellulase enzyme from Novozymes (Denmark).

See:

Zhang, Yi-Heng Percival, and Lee R. Lynd. "Toward an aggregated understanding of enzymatic hydrolysis of cellulose: noncomplexed cellulase systems." Biotechnology and bioengineering 88.7 (2004): 797-824;

Fan, L. T., Yong-Hyun Lee, and David H. Beardmore. "Mechanism of the enzymatic hydrolysis of cellulose: effects of major structural features of cellulose on enzymatic hydrolysis." Biotechnology and Bioengineering 22.1 (1980): 177-199;

Mandels, Mary, Lloyd Hontz, and John Nystrom. "Enzymatic hydrolysis of waste cellulose." Biotechnology and Bioengineering 16.11 (2004): 1471-1493;

Philippidis, George P., Tammy K. Smith, and Charles E. Wyman. "Study of the enzymatic hydrolysis of cellulose for production of fuel ethanol by the simultaneous saccharification and fermentation process." Biotechnology and bioengineering 41.9 (1993): 846-853;

Pääkkö, M., et al. "Enzymatic hydrolysis combined with mechanical shearing and high-pressure homogenization for nanoscale cellulose fibrils and strong gels." Biomacromolecules 8.6 (2007): 1934-1941;

Yang, Bin, and Charles E. Wyman. "BSA treatment to enhance enzymatic hydrolysis of cellulose in lignin containing substrates." Biotechnology and Bioengineering 94.4 (2006): 611-617;

Sun, Ye, and Jiayang Cheng. "Hydrolysis of lignocellulosic materials for ethanol production: a review." Bioresource technology 83.1 (2002): 1-11;

Saddler, J. N., et al. "Enzymatic hydrolysis of cellulose and various pretreated wood fractions." Biotechnology and bioengineering 24.6 (1982): 1389-1402;

Khodaverdi, Mandi, et al. "Kinetic modeling of rapid enzymatic hydrolysis of crystalline cellulose after pretreatment by NMMO." Journal of industrial microbiology & biotechnology (2012): 1-10;

Obama, Patrick, et al. "Combination of enzymatic hydrolysis and ethanol organosolv pretreatments: Effect on lignin structures, delignification yields and cellulose-to-glucose conversion." Bioresource Technology (2012);

Wiman, Magnus, et al. "Cellulose accessibility determines the rate of enzymatic hydrolysis of steam-pretreated spruce." Bioresource Technology (2012);

Elliston, Adam, et al. "High concentrations of cellulosic ethanol achieved by fed batch semi simultaneous saccharification and fermentation of waste-paper." Bioresource Technology (2013);

Kinnarinen, Teemu, et al. "Effect of mixing on enzymatic hydrolysis of cardboard waste: Saccharification yield and subsequent separation of the solid residue using a pressure filter." Bioresource technology (2012);

Wang, Lei, Richard Templer, and Richard J. Murphy. "High-solids loading enzymatic hydrolysis of waste papers for biofuel production." Applied Energy (2012);

Li, Sujing, Xiaonan Zhang, and John M. Andresen. "Production of fermentable sugars from enzymatic hydrolysis of pretreated municipal solid waste after autoclave process." Fuel 92.1 (2012): 84-88;

Dubey, Alok Kumar, et al. "Bioethanol production from waste paper acid pretreated hydrolyzate with xylose fermenting *Pichia stipitis*." Carbohydrate Polymers (2012);

Kinnarinen, Teemu, et al. "Solid-liquid separation of hydrolysates obtained from enzymatic hydrolysis of cardboard waste." Industrial Crops and Products 38 (2012): 72-80;

Nørholm, Nanna Dreyer, Jan Larsen, and Frank Krogh Iversen. "Non-pressurised pretreatment, enzymatic hydrolysis and fermentation of waste fractions." U.S. patent application Ser. No. 13/405,262;

Das, Arpan, et al. "Production of Cellulolytic Enzymes by *Aspergillus fumigatus* ABK9 in Wheat Bran-Rice Straw Mixed Substrate and Use of Cocktail Enzymes for Deinking of Waste Office Paper Pulp." Bioresource technology (2012);

Chen, Hui, et al. "Enzymatic Hydrolysis of Recovered Office Printing Paper with Low Enzyme Dosages to Produce Fermentable Sugars." Applied biochemistry and biotechnology (2012): 1-16;

Yan, Shoubao, et al. "Fed batch enzymatic saccharification of food waste improves the sugar concentration in the hydrolysates and eventually the ethanol fermentation by *Saccharomyces cerevisiae* H058." Brazilian Archives of Biology and Technology 55.2 (2012): 183-192;

Arora, Anju, et al. "Effect of Formic Acid and Furfural on the Enzymatic Hydrolysis of Cellulose Powder and Dilute Acid-Pretreated Poplar Hydrolysates." ACS Sustainable Chemistry & Engineering 1.1 (2012): 23-28;

Wang, Lei, et al. "Technology performance and economic feasibility of bioethanol production from various waste papers." Energy & Environmental Science 5.2 (2012): 5717-5730;

Vazana, Yael, et al. "Designer Cellulosomes for Enhanced Hydrolysis of Cellulosic Substrates." Cellulases (2012): 429;

Van Dyk, J. S., and B. I. Pletschke. "A review of lignocellulose bioconversion using enzymatic hydrolysis and synergistic cooperation between enzymes-Factors affecting enzymes, conversion and synergy." Biotechnology Advances (2012);

Menind, A., et al. "Pretreatment and usage of pulp and paper industry residues for fuels production and their energetic potential." International Scientific Conference Biosystems Engineering, Tartu, Estonia, 10-11 May 2012. Vol. 10. No. Special Issue I. Estonian Research Institute of Agriculture, 2012;

Han, Lirong, et al. "Alkali pretreated of wheat straw and its enzymatic hydrolysis." Brazilian Journal of Microbiology 43.1 (2012): 53-61;

Holm, Jana, et al. "Pretreatment of fibre sludge in ionic liquids followed by enzyme and acid catalysed hydrolysis." Catalysis Today (2012), each of which is expressly incorporated herein by reference.

See also, US Pub. Pat. Appl. 20120329096; 20120322117; 20120283164; 20120282666; 20120282239; 20120184020; 20120184007; 20120171732; 20120115192; 20120097194; 20120094340; 20110306101; 20110306100; 20110300585; 20110275118; 20110250646; 20110229959; 20110224416; 20110201093; 20110195481; 20110183396; 20110165661; 20110165660; 20110146142; 20110129886; 20110117067; 20110039318; 20100304420; 20100291653; 20100279354; 20100221819; 20100199548; 20100196981; 20100189706; 20100075404; 20100071259; 20100068768; 20100003733; 20090318571; 20090317864; 20090298149; 20090209009; 20090170174; 20090137438; 20090056707; 20090056201; 20090053800; 20090053777; 20090050134; 20090004714; 20080227182; 20080227161; 20080193992; 20080102502; 20080064064; 20070241306; 20070227971; 20070221552; 20070218541; 20070207939; 20070199903; 20070175825; 20070072185; 20070037259; 20070031953; 20070031919; 20070031918; 20060246563; 20060154352; 20050244934; 20050148056; 20050129643; 20050118130; 20050075497; 20030211958; 20030203466; 20030022347; 20030013172; 20020195213; 20020164731; and U.S. Pat. Nos. 8,338,139; 8,318,461; 8,309,331; 8,304,219; 8,287, 732; 8,273,181; 8,263,368; 8,247,203; 8,227,236; 8,222, 010; 8,202,709; 8,187,860; 8,114,974; 8,105,398; 8,093, 037; 8,053,566; 7,998,713; 7,960,153; 7,932,063; 7,910, 338; 7,846,705; 7,819,976; 7,807,419; 7,781,191; 7,727,746; 7,670,813; 7,625,728; 7,585,652; 7,566,561; 7,344,876; 7,183,093; 7,109,005; 6,942,754; 6,663,780; 6,623,948; 6,566,114; 6,528,298; 6,399,351; 6,361,989; 6,309,871; 6,074,856; 5,888,806; 5,736,032; 5,733,758; 5,589,164; 5,587,157; and 5,352,444, each of which is expressly incorporated herein by reference in its entirety.

DETAILED DESCRIPTION OF THE PREFERRED EMBODIMENTS

Figure 1:
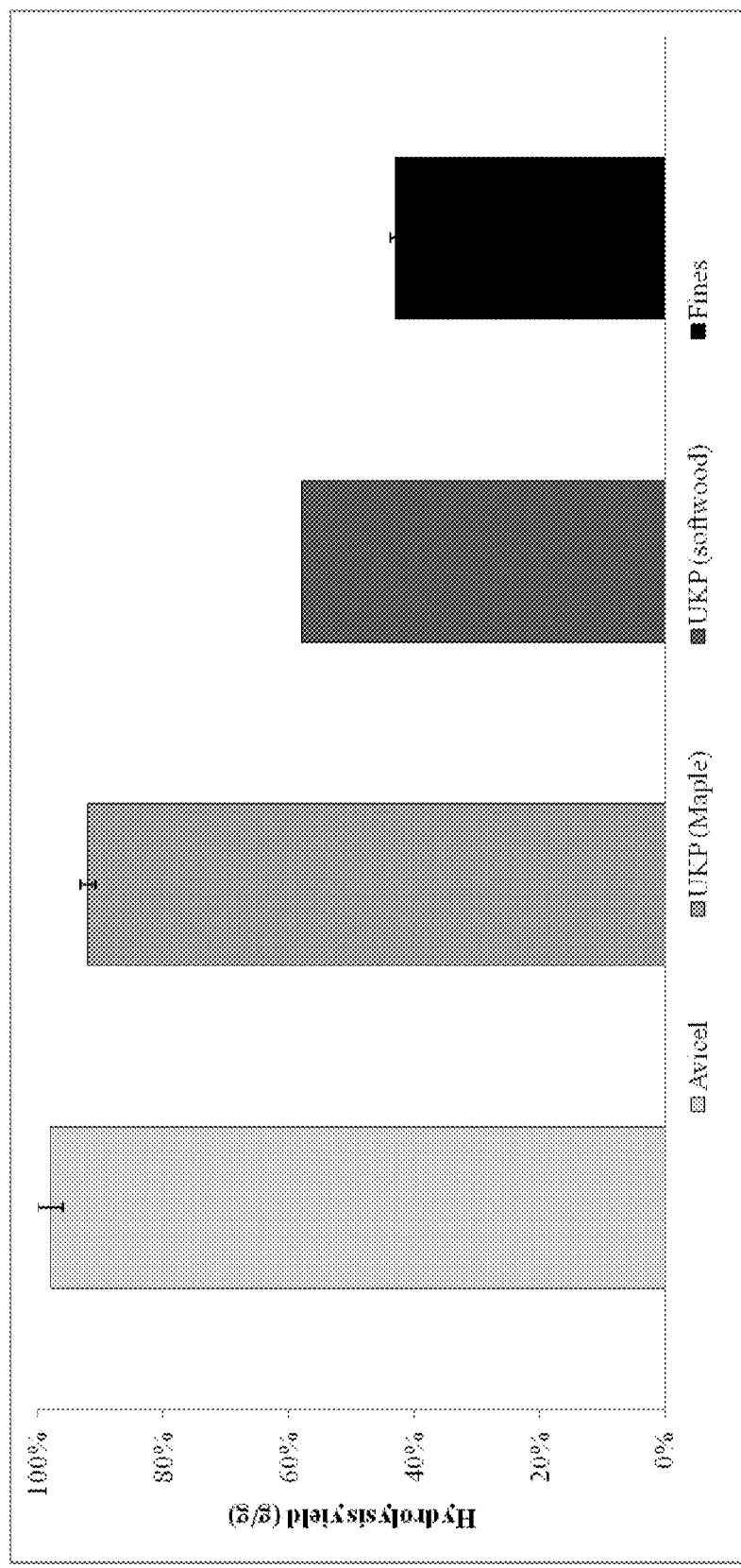
FIG. 1 shows enzymatic hydrolysis yield of different substrates. Enzyme was added 50 FPU of *T. reesei* and the hydrolysis was conducted at 50° C. for 3 days.

Material and Methods
Raw Materials

The fines were procured from a NYS based recycled linerboard-manufacturing mill. Additionally a comparative study was undertaken where commercial OCC boxes were repulped and hydrolyzed using commercial cellulases. Unbleached softwood kraft pulp (USKP), an unbleached hardwood kraft pulp (UHKP) and mixtures of fiber and fillers were used for hydrolysis. Recycled OCC was prepared by simple slushing of OCC boxes and dispersion. Pulps were ground and screened through a 200 mesh screen (such that the accepts were less than 75 μm in size).

Samples of commercially available cellulases were obtained—*Aspergillus Nigra*, and *Trichoderma Reesei*.
Fines Analysis pH meter 2500 series of Cole Parmer® was used for evaluating pH of fines and hydrolysate. Solid content and ash content was computed according to the National Renewable Energy Laboratory (NREL) Laboratory Analytical Procedure (LAP, NREL/TP-510-42627, NREL/TP-510-42622). Enzyme activity was also determined by NREL LAP (NREL/TP-510-42628). Particle size and Zeta potential were defined by a particle size analyzer (90 Plus/BI-MAS, Brookhaven Instruments Co.)
Enzymatic Hydrolysis The hydrolysis of fines was carried in a medium with a solid to liquid ratio of 1:20 with a cellulase dosage of 5-100 FPU using 20 mL sodium acetate buffer. A commercial grade enzyme (C2730, derived from the fungus *Trichoderma reesei* ATCC 26921) was procured from Sigma Aldrich. The hydrolysis flask was placed in a shaking incubator (Reciprocal Shaking Bath 51221080, Precision Co.,) and hydrolyzed at 50° C. for 72 h at 100 rpm. The solid residue was recovered by filtration with filter paper (Whatman No. 1) and the hydrolysis yield calculated with the weight of sugars divided by total weight of biomass load. Sugar content was analyzed by HPLC.
Filler Effect To determine effect of filler on hydrolysis yield pulp reject mixtures were generated in the lab composed of unbleached softwood kraft pulp (UKP) mixed with various proportions of Calcium Carbonate and Kaolin. The filler content was varied to understand the influence of each on hydrolysis yield. Imitating the total filler content in original fines, the proportions of calcium carbonate and kaolin were adjusted to a total of 30% (w/w) and the ratio of fillers was varied between 0-30%.
Surfactant Effect Since fillers provide adsorption surfaces for the cellulase enzymes which are nonproductive in terms of sugar production, one method of inactivation is to shield their surfaces with a suitable surfactant to prevent enzyme adsorption. A cationic and a nonionic surfactant were chosen for this purpose. Cetyl trimethyl ammonium bromide (CTAB, Catalog No. Alfa Aesar, Ward Hill Mass.) was obtained in powder form and stock solutions of 1% w/w in double distilled water were prepared. Similar solutions of a non-ionic surfactant, Tween-80 were also prepared.
Enzyme Hydrolysis Experiments Samples of the raw material (fines or waste rejects) were preweighed to 1 g dry weight and placed in 100 ml conical flasks provided with magnetic stirrers. Surfactants were also dosed followed by the cellulase mixtures in the required dosages. The flasks were shaken in a water bath for varying times upto 48 h and were removed at different time intervals. The hydrolyzed material was then filtered through 0.1 um filters and the filtrates were taken as the hydrolyzates for yield and compositional analysis by HPLC and 1NMR techniques. The solid residues were dried in an oven and the weights were used in the overall hydrolysis yield calculations. The solid residues were dissolved in 1% sulfuric acid and subsequently filtered again to determine the acid soluble (presumably CaCO$_3$) contents of the minerals. The remaining insoluble residue was taken to represent Kaolin.
Results Table 1 shows the characteristics of fines from the waste rejects of a recycled linerboard mill repulping OCC. The solids were obtained from a screw presses at a consistency (oven dry mass of solids/total mass) of 35%, the remainder being water. The average particle size was 2.1 μm. It is likely that the larger particles correspond to fragments of fibers whereas the smaller ones correspond to fillers and other mineral debris in the suspensions. The zeta potential is slightly negative. The higher levels of calcium carbonate and kaolin in the minerals originate most likely from deinking of white paper containing fillers or coated grades of paper. The total ash content was significant consisting 33% (g/g) of fines and Calcium Carbonate (CaCO$_3$) composed around half of this ash. Lignin was also contained in the fines at 3%.

The particle size of fines was around 3 μm and the pH was close to neutral (6.4), but the zeta potential was quite low (−9 mV).

The hydrolysis yields of Avicel, UKP-maple (non-dried), UKP-softwood (dried) and paper mill fines rejects were compared (FIG. 1). Avicel is a microcrystalline cellulose and when subjected to hydrolysis, nearly all of the cellulose was readily converted into monomeric glucose. Similarly, the conversion of the sample of the unbleached kraft (hardwood) pulp was extremely high. This pulp was laboratory prepared (kappa number of 18) and could also be depolymerized to greater than 90%. The softwood pulp sample was converted to yield only 60%, probably due to a larger hemicellulose content. Unbleached kraft softwood pulp shows lower yields primarily because this pulp was dried and reslushed before enzymatic hydrolysis. The process of drying causes the pulps to hornify i.e. limit the accessibility of cellulose by reducing the cell wall porosity. Upon reslushing therefore, a dried pulp fiber will not rehydrate to the same extent as virgin fibers and the cellulases are blocked from entering the crystalline structure to cause hydrolysis. The lowest hydrolysis yield was found for the mill fines rejects; around 0.4 g of sugars from 1 g of fines (OD) among the four substrates.

Figure 2:
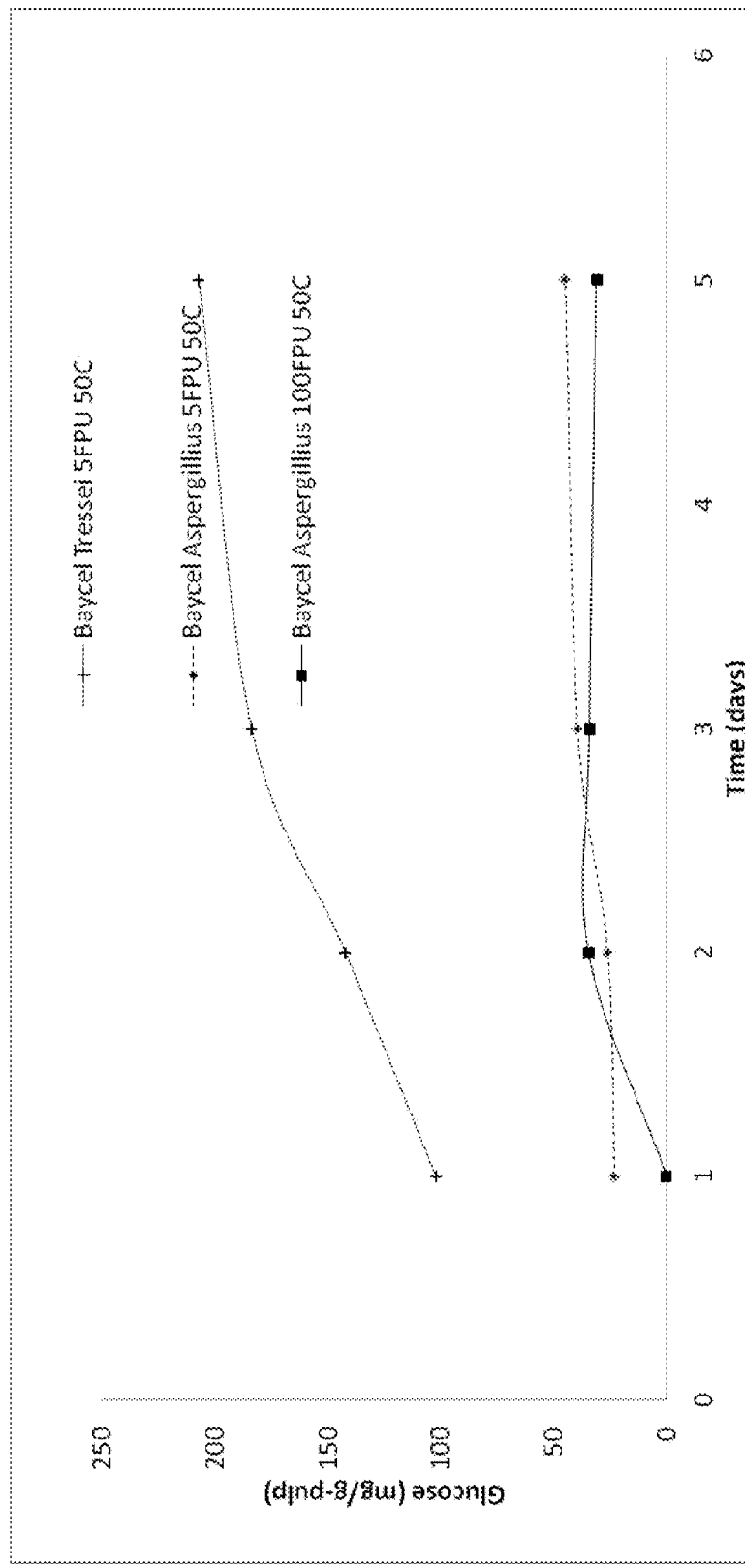
FIG. 2 shows enzymatic hydrolysis yield of a bleached hardwood kraft pulp (*Eucalyptus*, Baycel). Different enzyme formulations.

Fillers inhibit hydrolysis in different ways. One of their primary actions is to competitively bind the cellulases thus rendering a significant fraction of the hydrolytics nonproductive. The effect of such fillers on enzyme hydrolysis is shown in FIG. 2. For this experiment, UKHWP was mixed with 30% of kaolin and $CaCO_3$ (PCC) in order to make the composition similar to fines and the hydrolysis yield was measured as a function of enzyme dosage (in FPU). The inhibitory effect is different between Kaolin and $CaCO_3$ and $CaCO_3$ had a higher inhibitory potential which decreased enzymatic hydrolysis yield.

Figure 3:
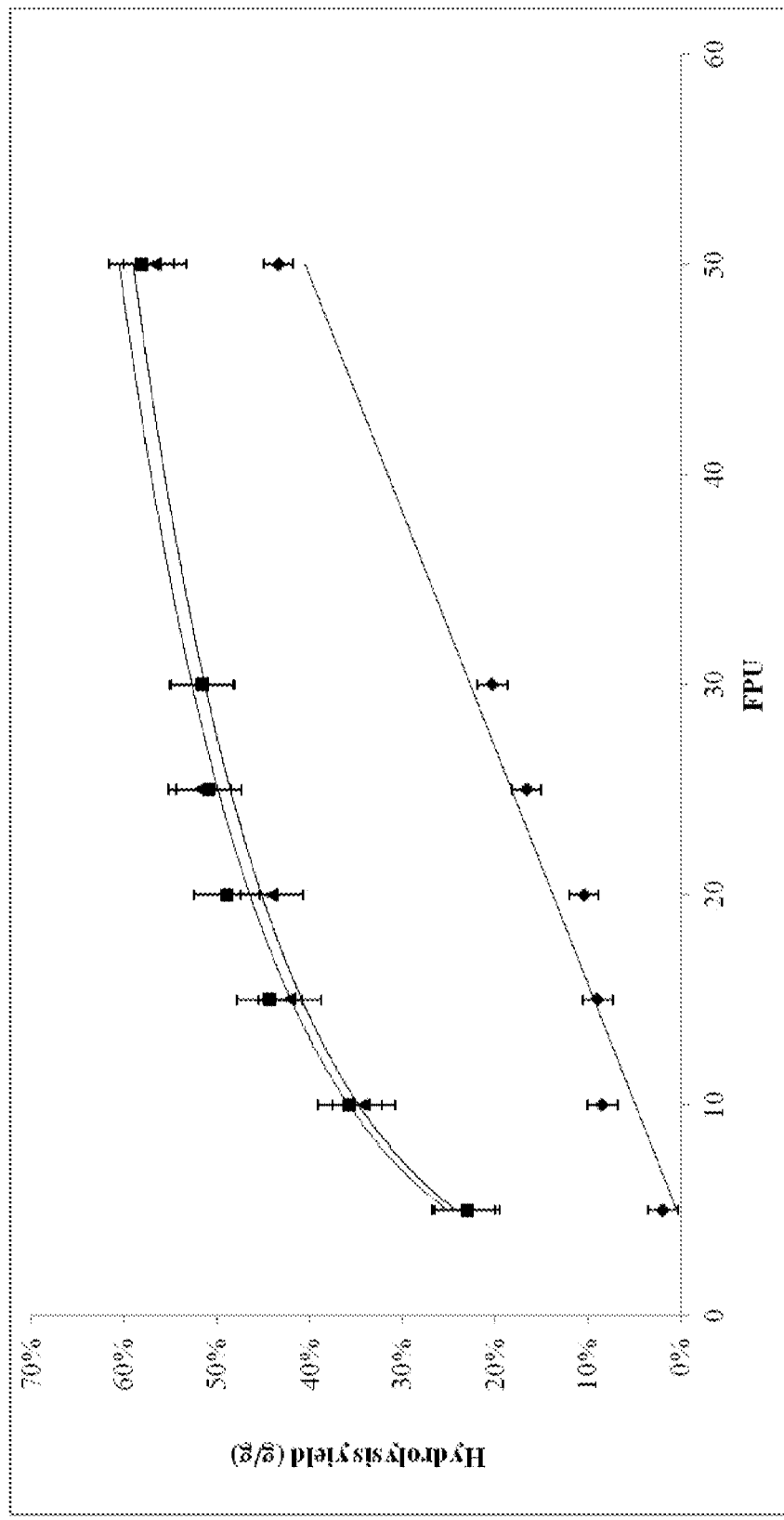
FIG. 3 shows the filler effect on UKP hydrolysis yield. UKP (■), UKP with 30% of Kaolin (▲), UKP with 30% of CaCO3 (♦) and replication n=2, α=0.05.

FIG. 2 shows the glucose yields for two different enzyme mixtures on a sample of bleached kraft hardwood pulp (*Eucalyptus*). The *Trichoderma reesei* enzyme was more effective and the *Aspergillus niger* did not show much activity. Fillers can reduce the yield of sugar simply by their interference with the enzyme action. Most often, their action can be simple competitive adsorption of the enzymes reducing the net activity. The impact of mineral fillers was demonstrated in the present study by mixing kaolin or calcium carbonate filler with unbleached hardwood kraft pulps and subjecting them to hydrolysis. The hydrolysis yield was measured for several enzyme dosages. The results shown in FIG. 3, indicate that calcium carbonate particles have a dramatic impact, reducing hydrolysis yields as compared to kaolin which was minimally active. It appeared that the calcium carbonate fillers could adsorb large amounts of the enzyme.

Figure 4:
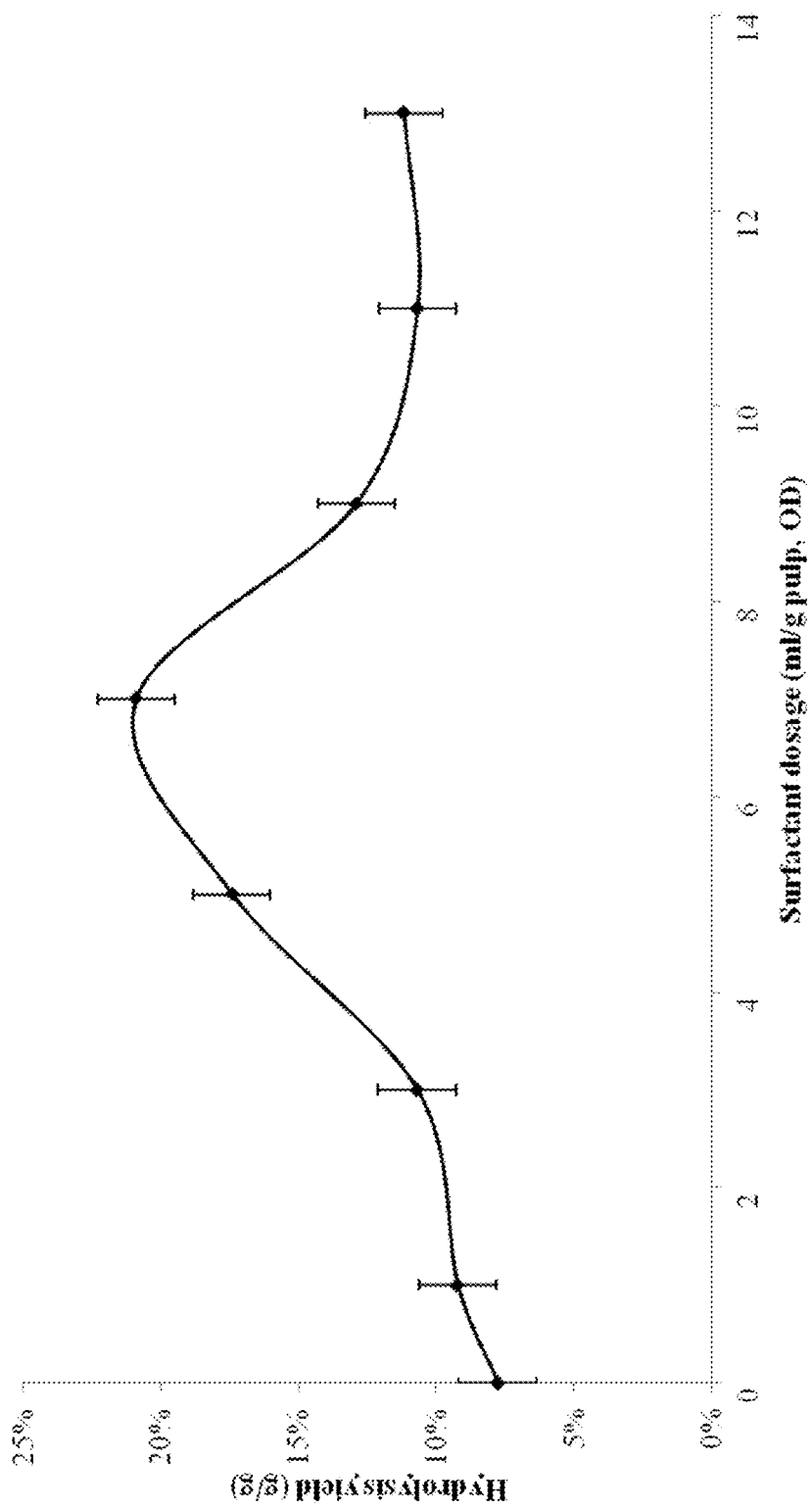
FIG. 4 shows hydrolysis yield of UKP and CaCO3 (15%) mixture depending on different Tween-80 dosage with 20 FPU of *T. reesei*
Figure 5:
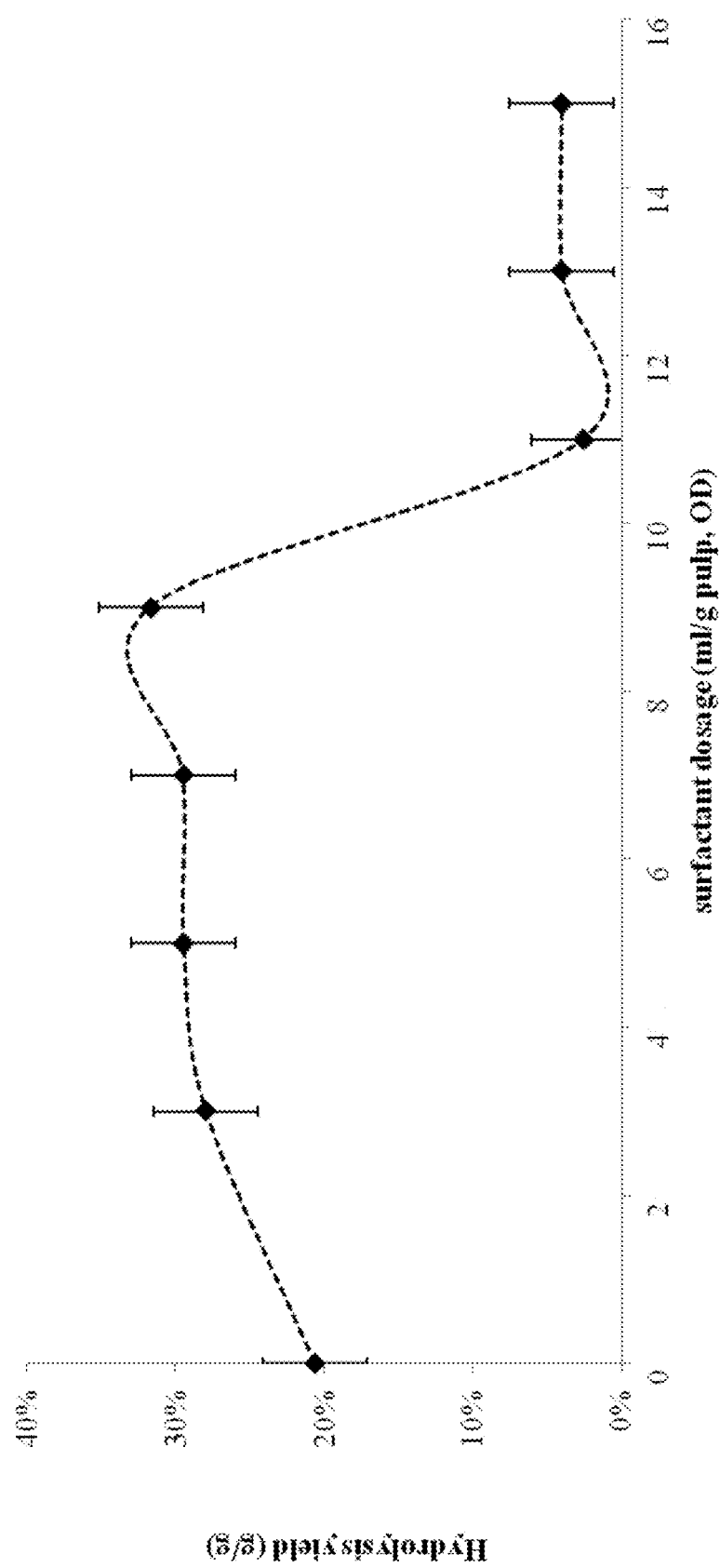
FIG. 5 shows hydrolysis yield of fines depending on different Tween-80 dosage with 20 FPU of *T. reesei*.

It may be possible to prevent the interference of hydrolysis by mineral particles by adsorbing a competitive molecule such as a surfactant. Calcium carbonate generally has cationic surfaces whereas charges on kaolin platelets are anionic on the basal surfaces. Kaolin particle edges also show positive charges within a narrow pH range around neutrality. Thus adsorption of ionic or nonionic surfactants could compete and block enzyme adsorption and inactivation by these minerals. We tested the performance of an uncharged (nonionic) surfactant at effecting the hydrolysis. The hydrolysis yield of UKP containing $CaCO_3$ (15%) was tested with 20 FPU in the range of 0-13% of the nonionic surfactant (Tween-80) dosage. The hydrolysis yield is shown in FIG. 4 as a function of surfactant dosage. The yield increased from 8% to 21% at the surfactant dosage of around 7%. It was observed that the surfactant dosage of lower than 4% and higher than 10% did not have impact for hydrolysis yield increase. Surfactant adsorption on $CaCO_3$ reaches a maximum at about the 7% level. Further addition results in the surfactant remaining in solution, possibly in micellar form and deactivating the enzymes, resulting in steep reductions in yields as observed beyond an optimal level (9%). FIG. 5 shows the impact of the nonionic surfactant on fines hydrolysis at different enzyme dosages. The yields difference was not significant and even low dosage, 3% of surfactant, obtained slightly higher hydrolysis yield in the range of low FPU.

Figure 6:
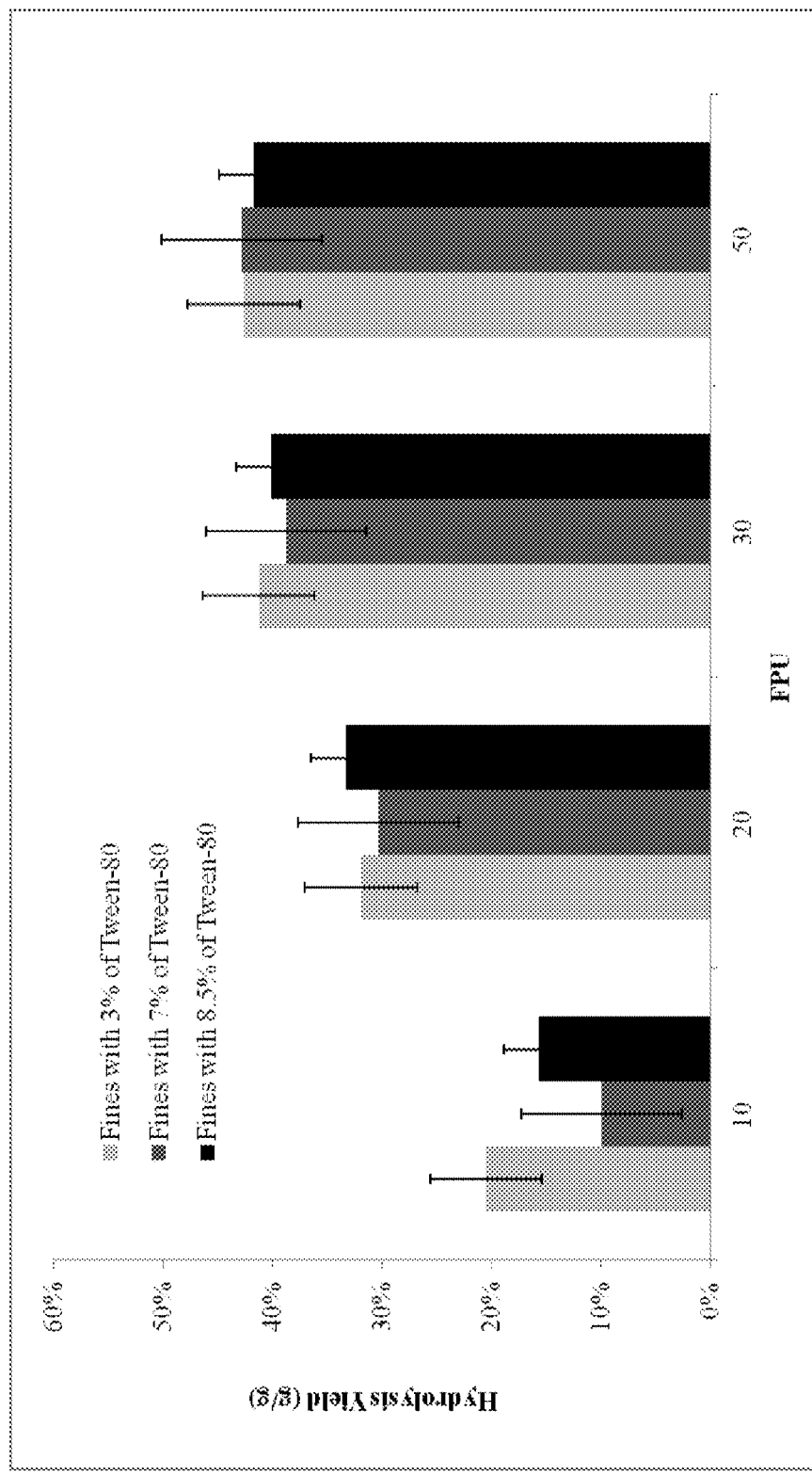
FIG. 6 shows hydrolysis yield of fines combined diverse dosage of Tween-80

The surfactant effect in relation to yield increase was measured with the artificial synthetic fines from UKP (softwood) mixture with $CaCO_3$ and Kaolin. These proportions of fillers in synthetic fines were to imitate the composition of OCC mill rejected fines. The hydrolysis yield of pulp containing fillers was increased with addition of 3% of the Tween-80 (FIG. 6).

Figure 7:
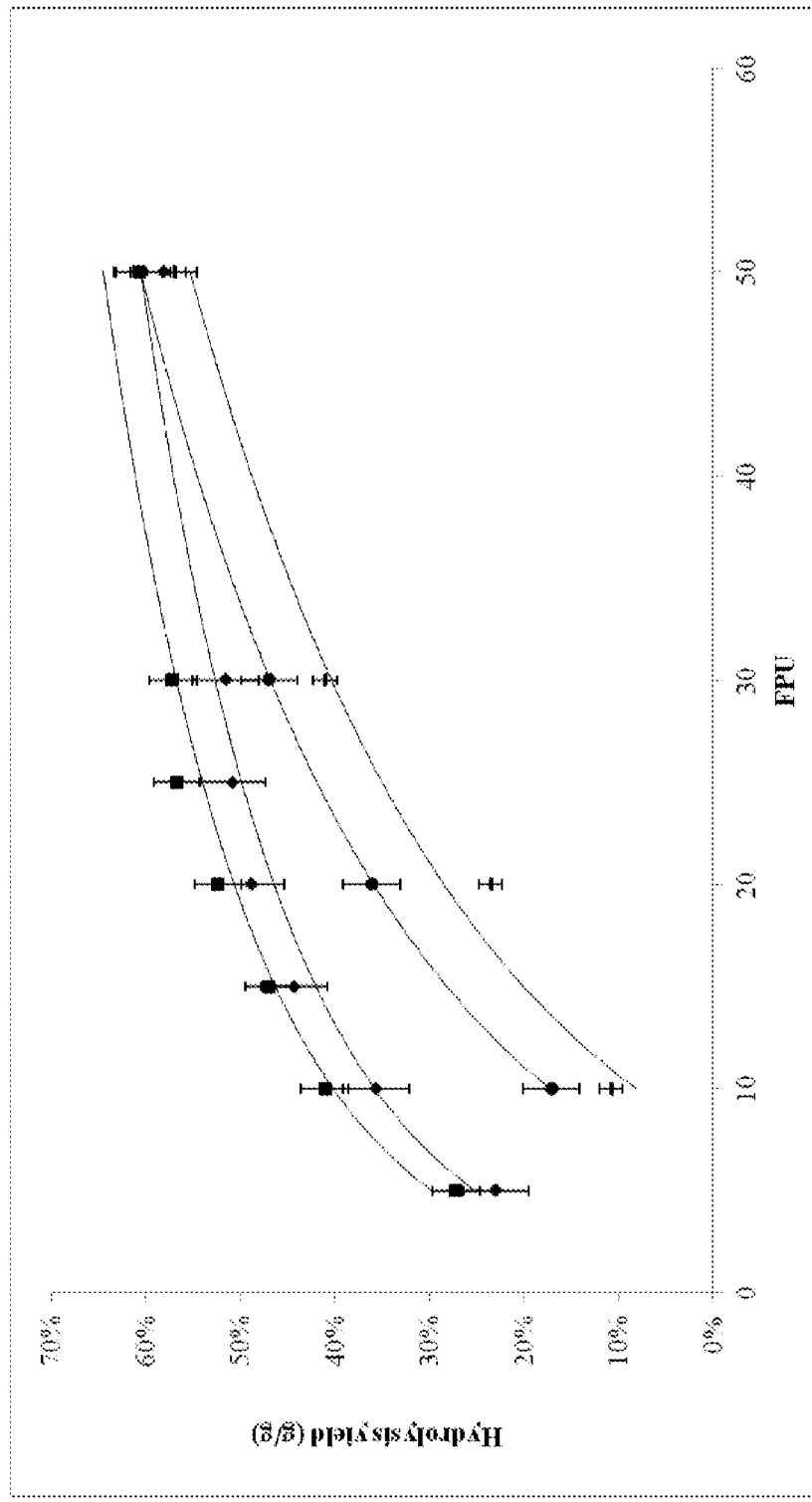
FIG. 7 shows Tween-80 (3%) effect on hydrolysis yield of UKP and mixture material of UKP and fillers. UKP (♦), UKP with Tween-80 (■), UKP+CaCO3 (15%)+Kaolin (15%) (−), UKP+CaCO3 (15%)+Kaolin (15%) with Tween-80 (•) and replication n=2, α=0.05.

FIG. 7 shows the impact of increasing enzyme dosage on the yield for enzymolysis of unbleached kraft pulp samples (at 48 h, taken to be the ultimate or equilibrium value). This figure displays the impact of the $CaCO_3$ and kaolin fillers, and a possible method of resolving their inhibition using the surfactant. The unbleached kraft pulp hydrolyzes effectively to 60% yields at high enzyme dosages (around 50 FPU). The addition of the surfactant boosts the yields and the enzyme kinetics significantly. When the $CaCO_3$ and kaolin fillers were included with the UKP (15% and 15%, by weight respectively), the hydrolysis kinetics fell dramatically although the final yield obtained was similar. The inclusion of the surfactant at the optimal dosage resulted in a significant boost to the kinetics and also increased hydrolysis yield.

Besides providing surfaces for competitive and nonproductive i.e. nonhydrolyzing sites for enzyme adsorption, the $CaCO_3$ could performing as an inhibitor in other important ways. For example, the presence of $CaCO_3$ alters the pH from the optimal value for hydrolysis and $Ca^{2+}$ ions could interfere in different ways. Charge neutralization and consequent coagulation of particles in the suspensions could occlude enzyme adsorption and thus present kinetic barriers to hydrolysis.

Figure 8:
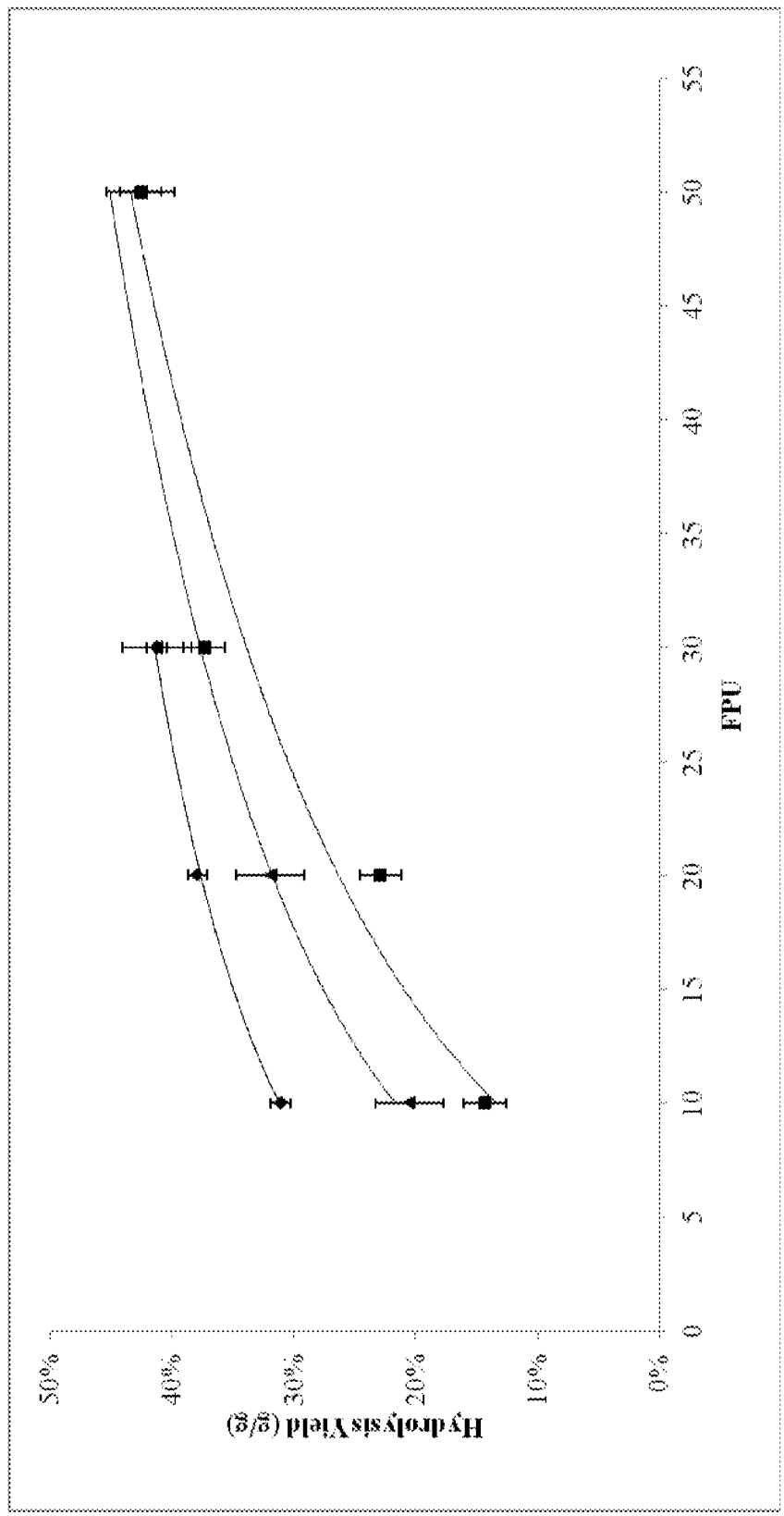
FIG. 8 shows a combination effect of Tween-80 (3%) and low pH buffer for hydrolysis yield. Fines only (■), Fines with 3% of Tween-80 (▲), Fines with Tween-80 and pH4 buffer (♦) and replication n=2, α=0.05.

Fine and pH 5 sodium acetate buffer compounds were varied with pH and buffer did not maintain the mixture pH 5 which was the optimal condition for cellulose. Using buffer around pH 5 is common for the enzymatic hydrolysis of cellulosic biomass in order to make the pH of solution stable and proper for enzyme. Addition of the pH 5 buffer to fines changed the pH of solution to around 6.5. The pH 6.5 of the solution was considered as improper initial condition for enzymatic hydrolysis. The buffer of pH 4 was tested and found the initial pH was reduced to 5.5 which was more close to optimal pH condition of the enzyme (pH 5). As the results, the lower pH buffer reinforced ability of enzymatic hydrolysis. Application of proper pH buffer and surfactant was an effective method to increase enzymatic hydrolysis and minimize enzyme dosage (FIG. 8).

The hydrolysis of the cellulosic substrates depends strongly on the accessibility of the internal structure of cellulose, but drying of cellulosic fibers/fines restricts the access to the hydrolytic enzymes (Hornification). Hornification is the result of drying of pulp fibers and fines that results in a loss of amorphous cellulose and reduction of the internal porosity both resulting in marked reduction of the pulp's hydration capacity, which increases pulp crystallinity. The impact of hornification of the fines by drying is quantified in the present study (Table 2). The drying effect i.e.

'hornification' seems to be responsible in reducing the cellulolytic yields by nearly 30% for both these substrates.

The presence of print ink can also be an inhibitory factor of enzymatic hydrolysis resulting in the difference between the yields of recycled pulp and virgin pulp. Printed and unprinted OCC were ground to a fine size to determine the decrease in hydrolysis yield. In the results, the gap of enzymatic hydrolysis yields of inked (44% g sugars/g OCC) and non-inked (46% g sugars/g OCC) was not significant.

Figure 9:
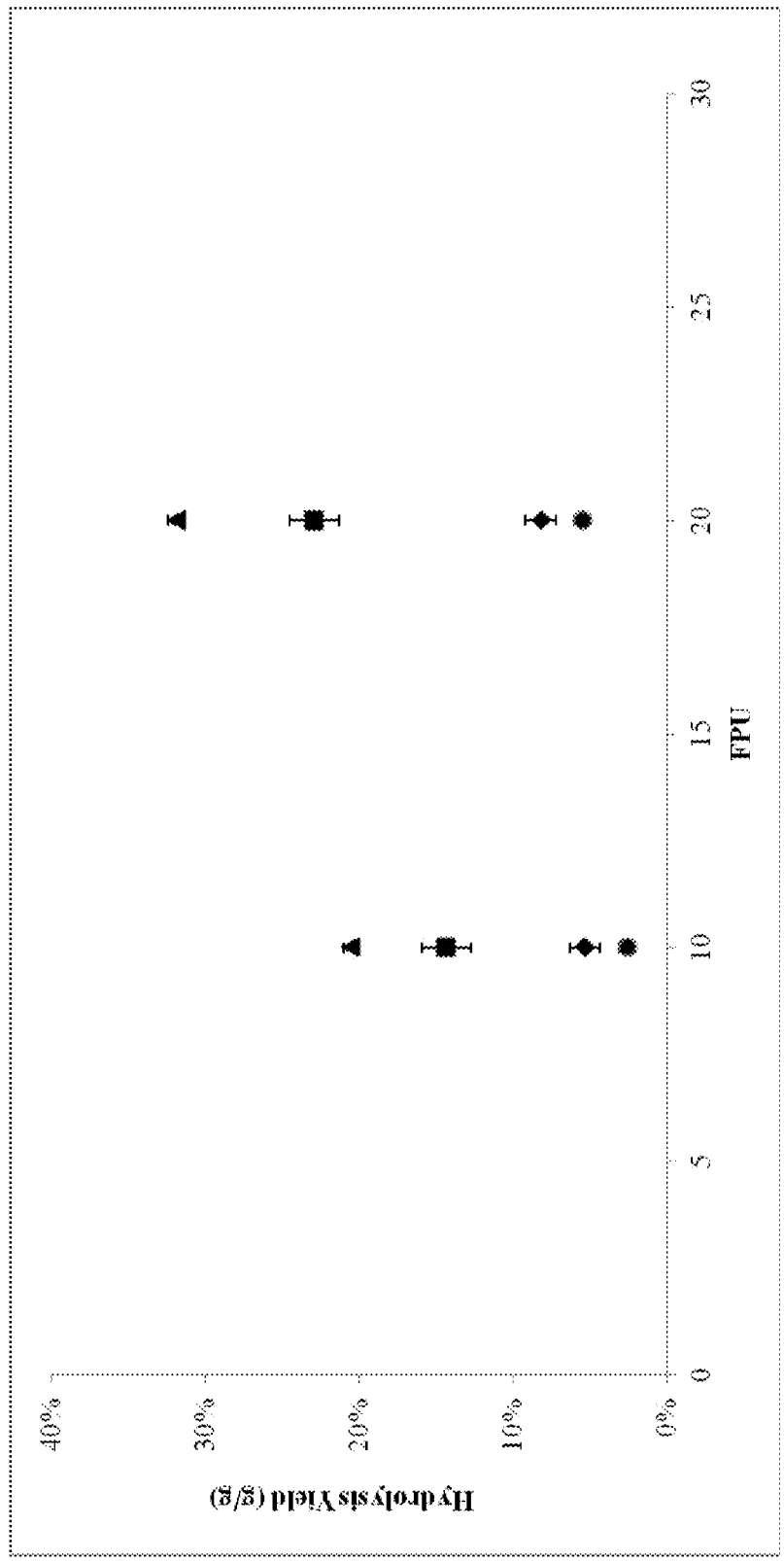
FIG. 9 shows a temperature effect on hydrolysis of pure fines and surfactant mixed fines. Fines with Tween-80 (3%) at 50° C. (▲), Fines at 50° C. (■), Fines at 55° C. (♦), Fines with Tween-80 (3%) at 55° C. (•) and replication n=2, α=0.05.

The hydrolysis yield peaked at 50° C. while further increase in temperature i.e. 55° C., decreased the hydrolysis yield due to degradation of cellulose. At this temperature, even surfactants failed to improve the hydrolysis yield (FIG. 9). At the lower temperature, 40° C., hydrolysis was decreased 15-20% compared to 50° C. (not-shown).

REFERENCES

Each of the following is expressly incorporated by reference in its entirety:

[1] Zhang Y-H P. Reviving the carbohydrate economy via multi-product lignocellulose biorefineries. Journal of industrial microbiology & biotechnology 2008; 35:367.

[2] Singh S, Mohanty A K, Sugie T, Takai Y, Hamada H. Renewable resource based biocomposites from natural fiber and polyhydroxybutyrate-co-valerate (PHBV) bioplastic. Composites Part A: Applied Science and Manufacturing 2008; 39:875.

[3] Galbe M, Zacchi G. A review of the production of ethanol from softwood. Applied Microbiology and Biotechnology 2002; 59:618.

[4] Kale G, Kijchavengkul T, Auras R, Rubino M, Selke S E, Singh S P. Compostability of bioplastic packaging materials: an overview. Macromolecular bioscience 2007; 7:255.

[5] FAOSTAT. 2011 Global Forest Products Facts and Figures.

[6] Villanueva A, Wenzel H. Paper waste-recycling, incineration or landfilling? A review of existing life cycle assessments. Waste Management 2007; 27:S29.

[7] Morris J. Recycling versus incineration: an energy conservation analysis. Journal of Hazardous Materials 1996; 47:277.

[8] Laurijssen J, Marsidi M, Westenbroek A, Worrell E, Faaij A. Paper and biomass for energy?: The impact of paper recycling on energy and CO2 emissions. Resources, conservation and recycling 2010; 54:1208.

[9] Scott G M, Smith A. Sludge characteristics and disposal alternatives for the pulp and paper industry. TAPPI International Environmental Conference: TAPPI Press; 1995, p. 269.

[10] Monte M, Fuente E, Blanco A, Negro C. Waste management from pulp and paper production in the European Union. Waste Management 2009; 29:293.

[11] He J, Lange C R, Dougherty M. Laboratory study using paper mill lime mud for agronomic benefit. Process Safety and Environmental Protection 2009; 87:401.

[12] Likon M, Saarela J. The Conversion of Paper Mill Sludge into Absorbent for Oil Spill Sanitation—The Life Cycle Assessment. Macromolecular Symposia: Wiley Online Library; 2012, p. 50.

[13] Fan Z, Lynd L R. Conversion of paper sludge to ethanol, II: process design and economic analysis. Bioprocess and biosystems engineering 2007; 30:35.

[14] Caputo A C, Pelagagge P M. Waste-to-energy plant for paper industry sludges disposal: technical-economic study. Journal of Hazardous Materials 2001; 81:265.

[15] Wang L, Sharifzadeh M, Templer R, Murphy R J. Bioethanol production from various waste papers: Economic feasibility and sensitivity analysis. Applied Energy 2012.

[16] Graf A, Koehler T. Oregon cellulose-ethanol study. An evaluation of the potential for eth-anol production in Oregon using cellulose-based feedstocks report prepared by the Oregon Of-fce of Energy Portland, Oreg., USA 2000.

[17] Lark N, Xia Y, Qin C-G, Gong C, Tsao G. Production of ethanol from recycled paper sludge using cellulase and yeast, *Kluveromyces marxianus*. Biomass and Bioenergy 1997; 12:135.

[18] Kádár Z, Szengyel Z, Réczey K. Simultaneous saccharification and fermentation (SSF) of industrial wastes for the production of ethanol. Industrial Crops and Products 2004; 20:103.

[19] Sun Y, Cheng J. Hydrolysis of lignocellulosic materials for ethanol production: a review. Bioresource Technology 2002; 83:1.

[20] Chen H, Venditti R A, Jameel H, Park S. Enzymatic Hydrolysis of Recovered Office Printing Paper with Low Enzyme Dosages to Produce Fermentable Sugars. Applied Biochemistry and Biotechnology 2012; 166:1121.

[21] Qing Q, Yang B, Wyman C E. Impact of surfactants on pretreatment of corn stover. Bioresource Technology 2010; 101:5941.

[22] Eriksson T, Borjesson J, Tjerneld F. Mechanism of surfactant effect in enzymatic hydrolysis of lignocellulose. Enzyme and Microbial Technology 2002; 31:353.

[23] Kurakake M, Ooshima H, Kato J, Harano Y. Pretreatment of bagasse by nonionic surfactant for the enzymatic hydrolysis. Bioresource Technology 1994; 49:247.

[24] Kapu N, Manning M, Hurley T, Voigt J, Cosgrove D, Romaine C. Surfactant-assisted pretreatment and enzymatic hydrolysis of spent mushroom compost for the production of sugars. Bioresource Technology 2012.

[25] Kim H J, Kim S B, Kim C J. The effects of nonionic surfactants on the pretreatment and enzymatic hydrolysis of recycled newspaper. Biotechnology and Bioprocess Engineering 2007; 12:147.

[26] Tanaka A, Hoshino E. Thermodynamic and activation parameters for the hydrolysis of amylose with *Bacillus* α-amylases in a diluted anionic surfactant solution. Journal of bioscience and bioengineering 2002; 93:485.

[27] Kristensen J B, Borjesson J, Bruun M H, Tjerneld F, Jorgensen H. Use of surface active additives in enzymatic hydrolysis of wheat straw lignocellulose. Enzyme and Microbial Technology 2007; 40:888.

[28] Pönni R, Kontturi E, Vuorinen T. Accessibility of cellulose: structural changes and their reversibility in aqueous media. Carbohydrate Polymers 2013.

[29] Chen Y, Wan J, Zhang X, Ma Y, Wang Y. Effect of beating on recycled properties of unbleached *eucalyptus* cellulose fiber. Carbohydrate Polymers 2012; 87:730.

What is claimed is:

1. A method for processing an aqueous stream of fines, comprising:
adding at least one surfactant to the aqueous stream of fines generated through a process of recycling old corrugated containerboards, and the aqueous stream comprises cellulosic fines which are rejected for recycling which have been separated from cellulosic fibers intended for recycling and papermaking fillers comprising calcium carbonate inorganic particles having an affinity for polysaccharide degradative enzymes, the at least one surfactant being added in an effective amount of between 3% to 10% by oven dry weight of the aqueous stream of fines, and the aqueous stream of fines lacks cellulose fibers suitable for papermaking;

adding at least one cellulose degrading enzyme to the aqueous stream of fines, in an amount sufficient to degrade at least a portion of the cellulosic fibers, to form an enzyme, surfactant, and fines-containing solution; and maintaining the enzyme, surfactant, and fines-containing solution for a sufficient period of time to degrade at least a portion of the cellulosic fibers into fermentable sugars, to achieve at least 10% hydrolysis yield by weight of fermentable sugars per weight of biomass of the fines, having an increased hydrolytic yield with respect to a hydrolysis yield of fermentable sugars per weight of biomass of the fines for the amount of the at least one cellulose degrading enzyme for degrading cellulosic fibers in the aqueous stream of fines in an absence of the at least one surfactant.

2. The method according to claim 1, wherein the aqueous stream of fines is from an old corrugated cardboard recycling facility, and wherein the aqueous stream of fines has 3% lignin by oven dry weight of the aqueous stream of fines.

3. The method according to claim 1, wherein the effective amount of between 3% to 10% is effective to absorb to the calcium carbonate inorganic particles to reduce an affinity of the calcium carbonate inorganic particles for the at least one cellulose degrading enzyme, and below a level which causes agglutination of the aqueous stream of fines.

4. The method according to claim 1, wherein the calcium carbonate inorganic particles comprise precipitated calcium carbonate.

5. The method according to claim 1, wherein the papermaking fillers further comprise kaolin.

6. The method according to claim 1, wherein the at least one polysaccharide degradative enzyme comprises at least one of a cellulase and a hemicellulase.

7. The method according to claim 1, wherein the at least one surfactant comprises polysorbate.

8. The method according to claim 1, wherein the at least one surfactant comprises polysorbate 80.

9. The method according to claim 1, wherein the hydrolysis yield by weight of fermentable sugars per oven dry weight of the cellulosic fibers of the fines is at least 40%.

10. A method for enzymatically hydrolyzing a mixed aqueous stream, comprising:

receiving the mixed aqueous stream which is a waste product from recycling old corrugated containerboards into paper products, the mixed aqueous stream containing cellulosic fines selectively rejected for recycling into paper products separated from cellulosic fibers retained for recycling and papermaking fillers comprising calcium carbonate inorganic particles from the old corrugated containerboards having a binding affinity for hydrolytic enzymes, and the mixed aqueous stream lacks cellulosic fibers suitable for papermaking;

adding at least one surfactant to the mixed aqueous stream in an amount of between 3% and 10% by oven dry weight of the mixed aqueous stream;

adding at least one cellulose hydrolytic enzyme having a binding affinity for the calcium carbonate inorganic particles, and which are inhibited by binding to the calcium carbonate inorganic particles, to the mixed aqueous stream in an amount sufficient to degrade the cellulosic fines, wherein the at least one surfactant in the amount between 3% and 10% is effective to reduce the binding affinity of the at least one cellulose hydrolytic enzyme for the calcium carbonate inorganic particles; and hydrolyzing the cellulosic fines with the added at least one cellulose hydrolytic enzyme, to achieve a hydrolytic yield of at least 10% sugars per gram oven dry weight of the cellulosic fines, wherein the hydrolytic yield is increased by the addition of the at least one surfactant in the amount of between 3% and 10% as compared to the hydrolytic yield absent addition of the at least one surfactant in the amount of between 3% and 10%.

11. The method according to claim 10, wherein the cellulosic fines comprise 3% lignin by weight of the oven dry weight of the mixed aqueous stream.

12. The method according to claim 10, wherein the amount between 3% and 10% is effective to absorb to the calcium carbonate inorganic particles to reduce an affinity of the calcium carbonate inorganic particles for the at least one cellulose hydrolytic enzyme, and below a level which causes agglutination of the mixed aqueous stream.

13. The method according to claim 10, wherein the calcium carbonate inorganic particles comprise precipitated calcium carbonate.

14. The method according to claim 13, wherein the papermaking fillers further comprise kaolin.

15. The method according to claim 10, wherein the at least one cellulose hydrolytic enzyme comprises at least one of a cellulase and a hemicellulase.

16. The method according to claim 10, wherein the at least one surfactant comprises polysorbate.

17. The method according to claim 10, wherein the at least one surfactant comprises polysorbate 80.

18. The method according to claim 10, wherein the hydrolytic yield by weight of fermentable sugars per oven dry weight of the cellulosic fines is at least 40%.

19. A method for enzymatically hydrolyzing a mixed stream of cellulosic fines and papermaking fillers comprising calcium carbonate-containing inorganic particles, comprising:

receiving the mixed stream of cellulosic fines which is a waste from a recycled paper mill which recycles paper to retain cellulose fibers for papermaking, and the mixed stream of cellulosic fines does not containing cellulose fibers suitable for papermaking, along with the papermaking fillers comprising calcium carbonate-containing inorganic particles from recycling of the paper;

adding at least one surfactant to the mixed stream, in an amount of between 3% and 10% by weight per an oven dry weight of the mixed stream;

adding at least one cellulose hydrolytic enzyme, having a binding affinity for the calcium carbonate-containing inorganic particles, and being competitively inhibited by binding to the calcium carbonate-containing inorganic particles, to the mixed stream;

the amount of the at least one surfactant being sufficient to reduce the binding affinity of the at least one cellulose hydrolytic enzyme for the inorganic particles and the competitive inhibition of the at least one cellulose hydrolytic enzyme by the calcium carbonate-containing inorganic particles, insufficient to inhibit the at least one cellulose hydrolytic enzyme, and insufficient to agglomerate the mixed stream;

adding an acidifier to the mixed stream; and hydrolyzing the cellulosic fines with the at least one cellulose hydrolytic enzyme at a temperature of 40° C. or higher, wherein a hydrolytic yield of grams sugars per gram of cellulosic fines of at least 10% is achieved.

20. The method according to claim 19, wherein the at least one surfactant comprises polysorbate 80, the rejected cellulosic fines comprise 3% lignin by weight per an oven dry weight of the mixed stream, and the hydrolytic yield is at least 40%.

* * * * *